US009592328B2

(12) United States Patent
Jeevanandam et al.

(10) Patent No.: US 9,592,328 B2
(45) Date of Patent: *Mar. 14, 2017

(54) SKIN INTERFACE DEVICE FOR CARDIAC ASSIST DEVICE

(71) Applicant: NuPulse, Inc., Raleigh, NC (US)

(72) Inventors: Valluvan Jeevanandam, Chicago, IL (US); Roger William Snyder, New Braunfels, TX (US); Robert Smith, Raleigh, NC (US); Paul DeDecker, Clinton Township, MI (US)

(73) Assignee: NuPulse, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/041,402

(22) Filed: Feb. 11, 2016

(65) Prior Publication Data
US 2016/0158426 A1 Jun. 9, 2016

Related U.S. Application Data

(60) Division of application No. 14/476,656, filed on Sep. 3, 2014, now Pat. No. 9,265,871, which is a
(Continued)

(51) Int. Cl.
*A61M 1/12* (2006.01)
*A61M 1/10* (2006.01)

(52) U.S. Cl.
CPC ............ *A61M 1/122* (2014.02); *A61M 1/106* (2013.01); *A61M 1/1072* (2013.01); *A61M 1/1086* (2013.01); *A61M 1/125* (2014.02); *A61M 2205/3303* (2013.01); *A61M 2205/3576* (2013.01); *A61M 2205/52* (2013.01); *A61M 2230/04* (2013.01); *A61M 2230/20* (2013.01);
(Continued)

(58) Field of Classification Search
None
See application file for complete search history.

(56) References Cited

U.S. PATENT DOCUMENTS 3,964,470 A 6/1976 Trombley
4,038,625 A 7/1977 Tompkins et al.
(Continued)

FOREIGN PATENT DOCUMENTS

WO WO 2012/101267 A2 8/2012

OTHER PUBLICATIONS

International Search Report from Related International Application No. PCT/US2014/053943 (Sep. 3, 2014).

*Primary Examiner* — Brian T Gedeon
(74) *Attorney, Agent, or Firm* — DLA Piper LLP (US)

(57) ABSTRACT

A skin interface device ("SID") for a cardiac assist device, including a SID cap having a first housing, an annular sleeve, and a first annular winding disposed over said annular sleeve. The SID further includes a SID base having a second housing formed to include a tubular portion, a cylindrical member disposed in said tubular portion, and a second annular winding disposed around said cylindrical member. The SID cap is configured to be rotationally attached to said SID base. When the SID cap is attached to the SID base, the second annular winding is disposed within the first annular winding, and the relative positions of the first annular winding and the second annular winding are fixed both laterally and vertically.

22 Claims, 26 Drawing Sheets

Related U.S. Application Data continuation-in-part of application No. 14/017,109, filed on Sep. 3, 2013, now abandoned.

(52) U.S. Cl.
CPC ..... *A61M 2230/30* (2013.01); *A61M 2230/50* (2013.01)

(56) References Cited

U.S. PATENT DOCUMENTS

| | | | |
|---|---|---|---|
| 5,098,397 | A | 3/1992 | Svensson |
| 5,350,413 | A | 9/1994 | Miller |
| 5,782,645 | A | 7/1998 | Stobie et al. |
| 6,530,876 | B1 | 3/2003 | Spence |
| 7,632,263 | B2 | 12/2009 | Denoth et al. |
| 7,766,881 | B2 | 8/2010 | Reinmann |
| 8,066,628 | B1 * | 11/2011 | Jeevanandam ..... A61M 1/1072 600/17 |
| 8,152,769 | B2 | 4/2012 | Douglas et al. |
| 8,323,174 | B2 | 12/2012 | Jeevanandam et al. |
| 9,125,981 | B2 | 9/2015 | Mann |
| 2004/0249361 | A1 | 12/2004 | Denoth et al. |
| 2007/0191779 | A1 | 8/2007 | Shubayev |
| 2012/0108885 | A1 | 5/2012 | Jeevanandam et al. |
| 2013/0331638 | A1 | 12/2013 | Cameron |
| 2015/0157842 | A1 | 6/2015 | Gill |
| 2015/0258261 | A1 | 9/2015 | Novack |

* cited by examiner

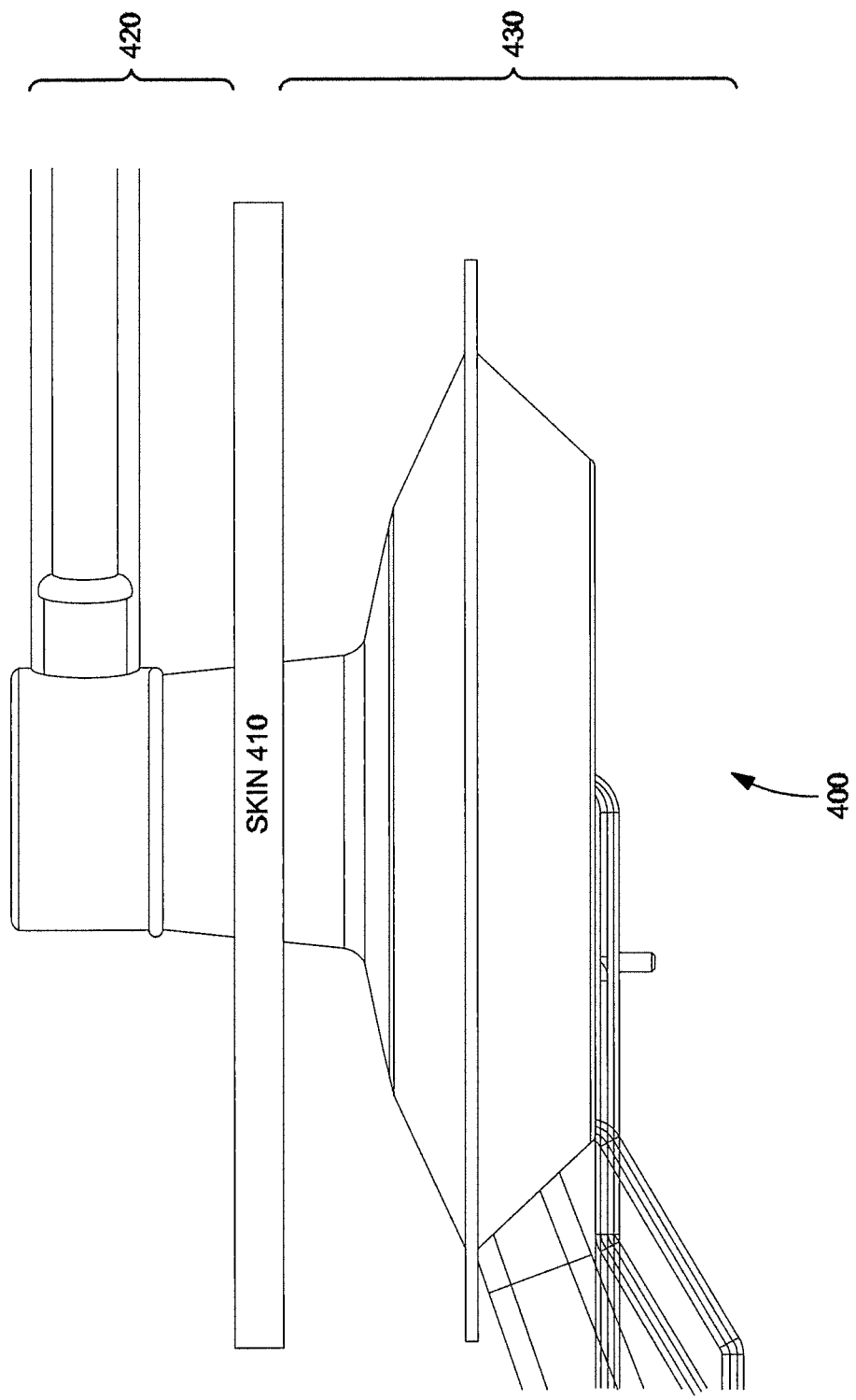

SKIN INTERFACE DEVICE FOR CARDIAC ASSIST DEVICE

CROSS-REFERENCE TO RELATED APPLICATIONS

This application is a divisional application of U.S. application Ser. No. 14/476,656 filed Sep. 3, 2014, now issued as U.S. Pat. No. 9,265,871; which is a continuation-in-part application of U.S. application Ser. No. 14/017,109 filed Sep. 3, 2013, now abandoned. The disclosure of each of the prior applications is considered part of and is incorporated by reference in the disclosure of this application.

BACKGROUND OF THE INVENTION

Field of the Invention

The invention is directed to assemblies, such as a skin interface device and an arterial interface device, and methods for implanting, positioning, and operating a cardiac assist device (CAD).

Background Information

The use of CADs is a well known method for treating heart failure. A pump is positioned inside the aorta, typically in the proximal descending aorta. The pump typically comprises a displacement volume of 40-50 cc, and works in series with the heart to augment blood flow. During diastole, the pump is inflated, thereby driving blood in the ascending aorta and aortic arch into the coronary arteries to supply oxygen to the heart muscle. During systole, as the left ventricle contracts, the pump is deflated so as to decrease the afterload.

Existing cardiac assist devices comprising pumps suffer from the problem of requiring inconvenient external apparatuses, such as for example an external tank filled with compressed gas and/or an external controller.

BRIEF DESCRIPTION OF THE DRAWINGS

The invention will be better understood from a reading of the following detailed description taken in conjunction with the drawings in which like reference designators are used to designate like elements as follows.

FIG. 4B illustrates a supracutaneous portion 420 and a subcutaneous portion 430 of Applicants' SID 400 when disposed within a patient.

DETAILED DESCRIPTION OF THE PREFERRED EMBODIMENTS

U.S. Pat. No. 8,323,174, having a common inventive entity herewith, and assigned to the common assignee hereof, is hereby incorporated by reference herein in its entirety.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Rather than using a containerized pressurized gas, such as for example helium gas, and the attendant tank, the inventors herein have taken a different approach. Using air instead of helium as a pumping medium means that there is always an infinite supply of pumping medium on hand. In certain embodiments, the air in the system can be replaced at regular intervals, or only when triggered, for instance by a humidity sensor. As such, when the air in the pump has become too moist, one can simply purge the air from the device and fill the device with relatively dry ambient air.

A much more portable system than presently available results from eliminating the need for both a helium tank and compressor.

The inflation/deflation cycles of a pump disposed in, for example, a patient's aorta can be triggered based on QRS complex detection from electrocardiogram (EKG) data, by dicrotic notch detection from pressure data, or by both. Electrodes and pressure sensors can be provided as necessary.

Deflation will typically be triggered based on the detection of a QRS complex, which indicates impending systole, while inflation will typically be triggered based on the detection of a dicrotic notch, which indicates the beginning of diastole.

Figure 1A:
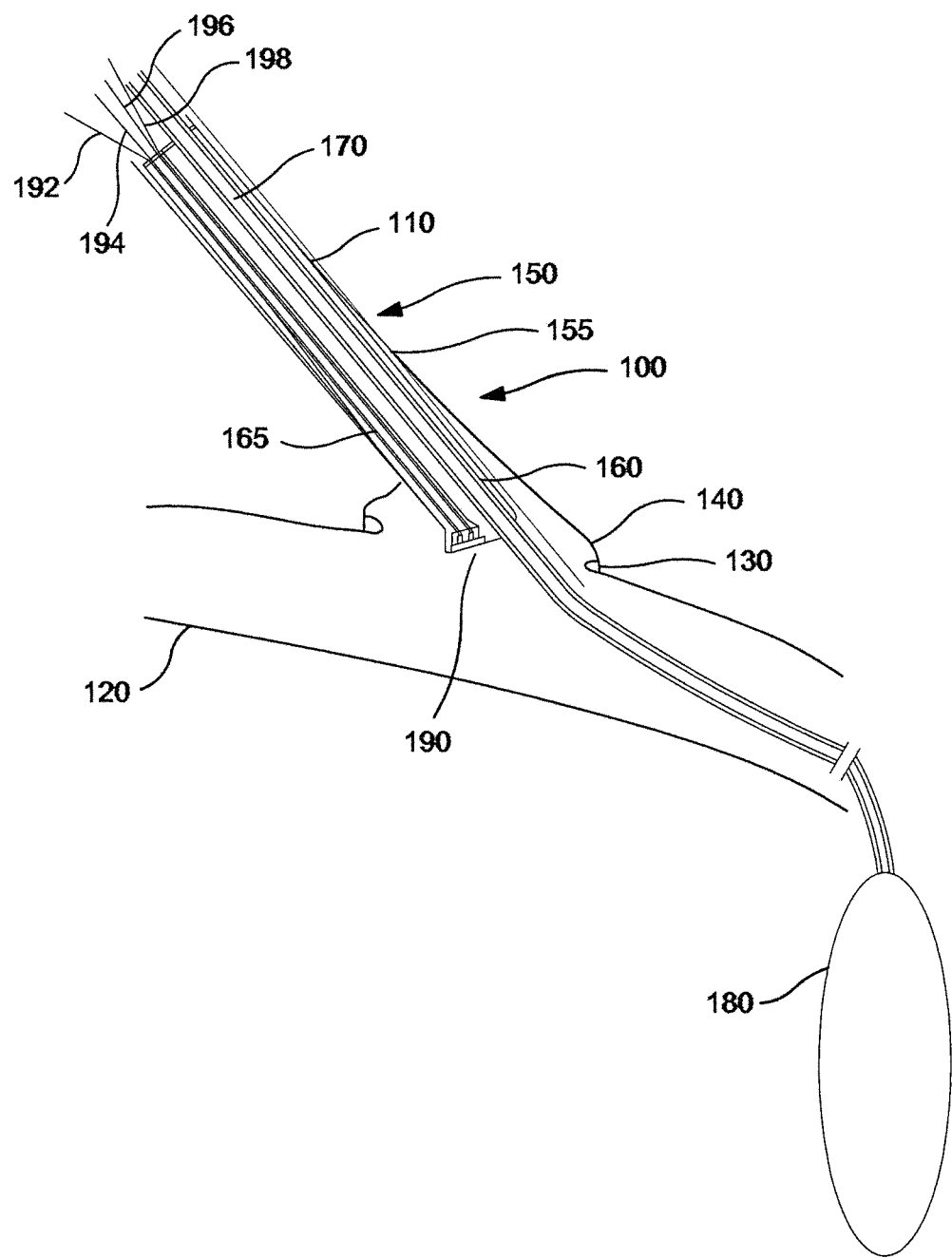
FIG. 1A schematically shows a CAD implanted in a patient using Applicants' arterial interface device ("AID") 150.
Figure 1B:
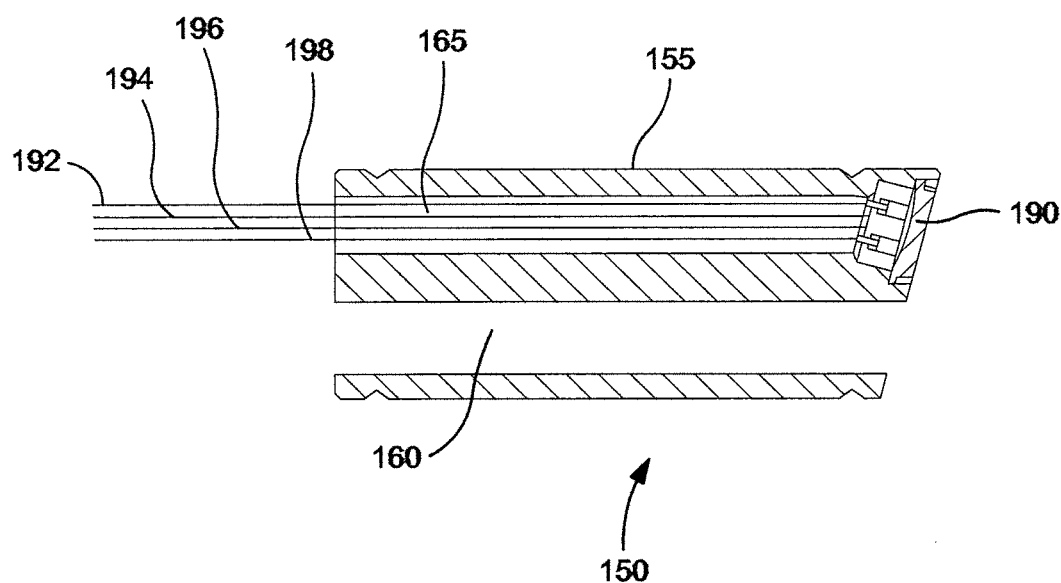
FIG. 1B is a cross-sectional view of AID 150.

FIGS. 1A and 1B illustrate Applicants' arterial interface device ("AID") 150. Referring to FIG. 1A, a vascular interface 100 is formed using a vascular graft 110 attached to an artery 120 with a suture ring 130 at the position of an incision in the artery. The particular graft shown flares at its distal end 140. AID 150 sits inside the graft 110, filling the interior of the graft 110.

Referring now to FIGS. 1A and 1B, AID 150 comprises a body 155. In certain embodiments, AID 150, including body 155 comprises silicon. In certain embodiments, body 155 comprises a polyurethane. In certain embodiments, body 155 comprises a polysiloxane. In the illustrated embodiment of FIGS. 1A and 1B, body 155 is formed to include two lumens extending therethrough. Lumen 160 is utilized to pass pneumatic drive line 170 through AID 150.

The second lumen 165 houses a pressure sensor 190 to measure arterial pressure, and sensor leads 192, 194, 196, and 198, to interconnect sensor 190 to Applicants' SID 400. Sensor leads 192, 194, 196, and 198, are used to provide power to sensor 190, provide a ground connection, to provide clock signals to sensor 190, and to communication arterial pressure signals from sensor 190 to SID 400.

The AID lumen through which the pump's drive line 170 passes is sized to fit snuggly on the perimeter of the driveline. This allows the surgeon to fix the location of the pump in the patient's aorta. In certain embodiments, AID 150 extends outwardly from the proximal end of the graft, to help minimize clot invasion. In certain embodiments, AID 150 is secured to and immobilized with respect to the graft.

Lumen 160 extends through the length of the AID 150 is filled by the pneumatic drive line 170. Pneumatic drive line 170 in turn is connected at its distal end to a pump 180. In certain embodiments, inflation catheter is formed to have an inner diameter in the range 3 to 6 mm (often about 5 mm), although other diameters are possible as well. In certain embodiments, the catheter will be (i) wide enough inside to lower resistance to fluid flow to the point that air can be used as the pressure medium, with a pressure source that need generate no more than 0.5 atmospheres in order to transmit pressure from the source to the pump, and (ii) narrow enough outside so that the presence of the inflation catheter in the various blood vessels does not significantly interfere with the flow of blood through the vessels. In this context, "narrow enough to avoid significant interference" means that the catheter occludes less than about 50 percent of the cross-sectional area of the vessel's lumen.

In certain embodiments, each component comprises one or more biocompatible materials, such as polytetrafluoroethylene (PTFE), expanded PTFE (ePTFE), polyurethane, polyethylene, polyethylene terephthalate, silicone, and/or titanium. In certain embodiments, pneumatic drive line 170 and/or pump 180 comprises a moisture resistant material to help prevent water passing through the pump wall and building up in the chamber. For example, in certain embodiments, moisture resistance is achieved by laminating a moisture resistant material onto or into the pneumatic drive line 170 and/or pump 180, or by applying a moisture-resistant coating to the inner or outer surface of the pump wall.

In certain embodiments, AID 150 is useful in other ways other than preventing the build-up of thrombus inside the graft 110. AID 150 can act as a cushion surrounding the pneumatic drive line 170 so as to help maintain the inflation catheter's patency when the graft is tied down. Also, the increased surface area of the AID 150 as compared to the pneumatic drive line 170 can ease the task of sealing the graft 110.

Not shown in FIG. 1A is the proximal end of the pneumatic drive line 170. Because the pump 180 needs to inflate and deflate in coordination with the cardiac cycle in order to function as a ventricular assist device, the pump must be in fluid communication with some sort of driver (e.g., an air compressor or pump) via the pneumatic drive line 170.

In embodiments wherein such a driver is external to the body, the Applicants' skin interface device ("SID") 400 (FIG. 4A) allows the design of the system to be composed of parts both implanted and external to the patient's body. The pneumatic drive line 170 is attached to SID 400, and SID 400 is attached to the fluid driver. In certain embodiments, the driver, the pneumatic drive line 170 and the pump 180 form a closed air system, wherein that closed system includes a well-defined and precisely controlled volume of air. Such a well-defined and precisely-controlled volume of air facilitates leak detection.

In certain embodiments, air volume and movement of air is precisely controlled using, for example and without limitation, a bellows driven by one or more linear actuators. In descriptions of Applicants' skin interface device herein, the pneumatic drive line 170 is alternatively referred to as an internal drive line.

To remove the pump 180 from its disposition within the aorta, AID 150 is detached from the graft 110. Because the AID 150 has prevented clots and other healing tissues from accumulating inside the graft 110, the AID 150 can be removed easily, leaving the graft 110 unblocked. The pump 180 can then be removed by pulling the pneumatic drive line 170 and pump 180 through the graft 110 lumen. A new pump can be advanced through the open graft 110 lumen along with a new AID 150. In this way, the pump can be replaced without having to remove and replace the graft 110.

Figure 2:
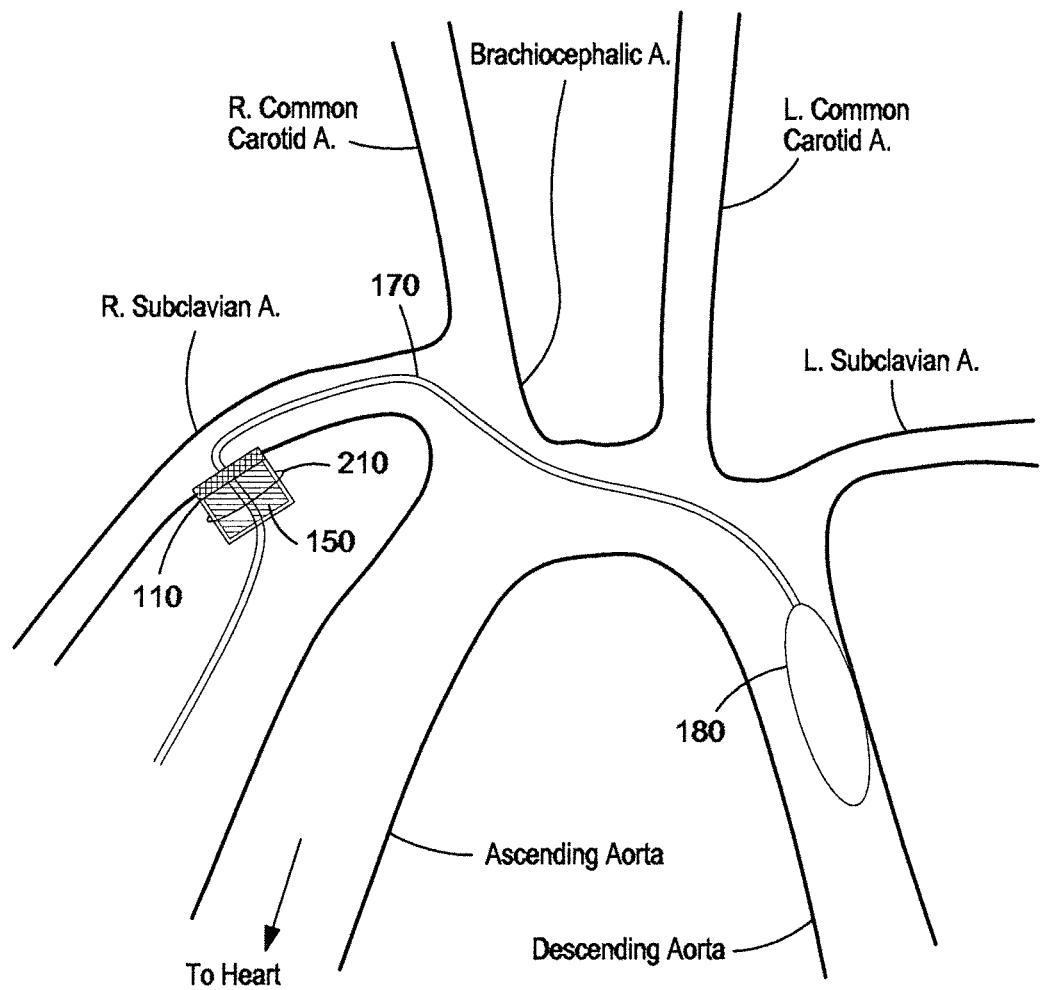
FIG. 2 schematically shows a pump positioned in the proximal descending aorta, with the pump's inflation catheter entering the vasculature at the right subclavian artery through Applicants' AID 150.

FIG. 2 shows (schematically) the graft 110 in position on the right subclavian artery. This position is advantageous because it allows easy surgical access and a relatively short distance to the descending aorta. FIG. 2 also shows the graft secured to the AID 150 by a suture 210. Other suitable positions for the interface include either common carotid artery, the brachiocephalic artery, the left subclavian artery, the descending aorta, and the abdominal aorta. Downstream branches of the aorta may also be used, such as the external iliac and femoral arteries.

Figure 3:
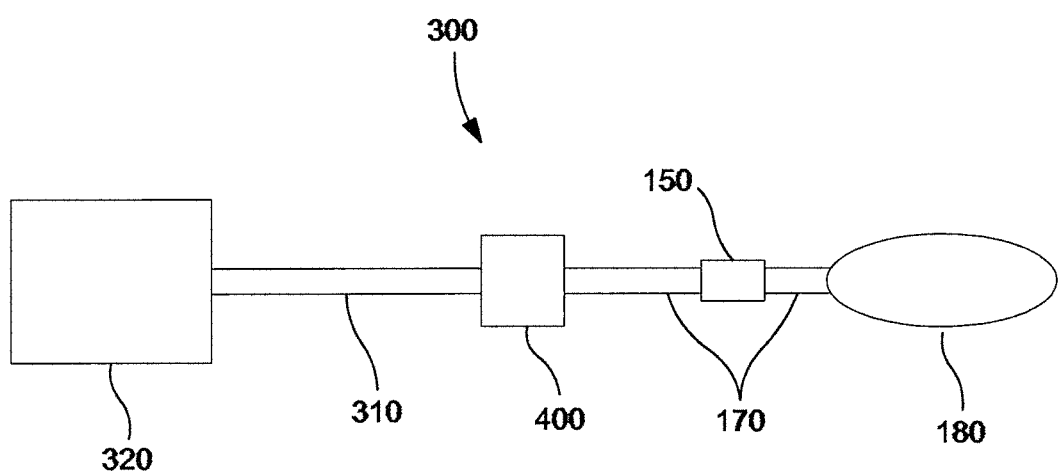
FIG. 3 schematically shows a cardiac assist device including an intra-aortic pump, an internal drive line, an arterial interface device, a skin interface device, an external drive line, and an external driver.

Referring now to FIG. 3, in certain embodiments Applicants' CAD comprises a pump 180, a pneumatic drive line 170, an AID 150, a SID 400, an external drive line 310, and an external driver 320.

In certain embodiments, pump 180 is sized and shaped to dangle inside a patient's aorta. In certain embodiments, the wall of the pump comprises moisture resistant material, or may be entirely moisture resistant, to keep the air inside the pump as dry as possible. One possible moisture resistant material for the pump comprises polyurethane. In certain embodiments, the one or more polyurethane polymers are modified to include surface silicone end groups.

At its proximal end, the pump 180 is connected to the distal end of the pneumatic drive line 170. An AID 150 is sized and shaped to pass the pneumatic drive line 170 through an arterial wall.

Applicants' SID 400 connects the proximal end of the pneumatic drive line 170 to the distal end of the external drive line 310. The proximal end of the external drive line 310 is connected to the driver 320.

The pump 180, the internal drive line 170, the SID 400, the external drive line 170, and the driver 320 can be charged with a pumping medium. In certain embodiments, the pumping medium comprises a fluid. A preferred pumping medium is air. In certain embodiments, pump 180, the pneumatic drive line 170, the SID 400, the external drive line 310, and the driver 320 define a closed fluid system. In certain embodiments, pump 180, the pneumatic drive line 170, the SID 400, the external drive line 310, and the driver 320 comprise an open system, wherein the bolus of air inside the system can be exchanged with the ambient environment.

As those skilled in the art will appreciate, pump 180 may have various sizes depending on the anatomy of the patient. In certain embodiments, pump 180 will typically have an inflated volume of about 40 to 60 cubic centimeters when inflated to 10 to 20 mmHg above the maximum systolic pressure.

In certain embodiments, sensors are connected to one or more communication interfaces that, like the pneumatic drive line 170, pass through the AID 150 and graft 110 and connect to Applicants' SID 400. In certain embodiments, these one or more communication interfaces provide data to a controller.

In certain embodiments, one or more sensors transmit data, by wire or wirelessly, to Applicants' SID 400. Examples of sensors include, without limitation, electrical leads to measure an electrocardiogram, sensors to detect body temperature, sensors to detect blood analytes (such as blood gases), sensors to detect intra-arterial pressure directly or indirectly, and/or sensors to measure humidity within pump 180. Indirect sensors include, for example and without limitation, a microphone to monitor heart sounds.

In certain embodiments, a controller 530 is disposed in SID 400. In certain embodiments, a controller 530 is integral with external driver 320.

In certain embodiments, signals from one or more sensors are used by controller 530 to monitor the cardiac cycle and, thereby, the counterpulsation cycle. In certain embodiments, combinations of signals from one or more sensors are used by controller 530 to monitor the cardiac cycle.

In certain embodiments, sensors are used to determine the state of the air inside the system. In certain embodiments, air pressure is measured to determine whether the pump is properly inflating, or if there is a leak in the system. In certain embodiments, data from the air pressure sensor is communicated to controller 530.

In certain embodiments, sensors for arterial blood pressure at the pump 180 and/or at the AID 150 are in communication with controller 530. In certain embodiments, these sensors communicate a detected arterial blood pressure to the controller 530, either by wire or wirelessly.

Figure 4A:
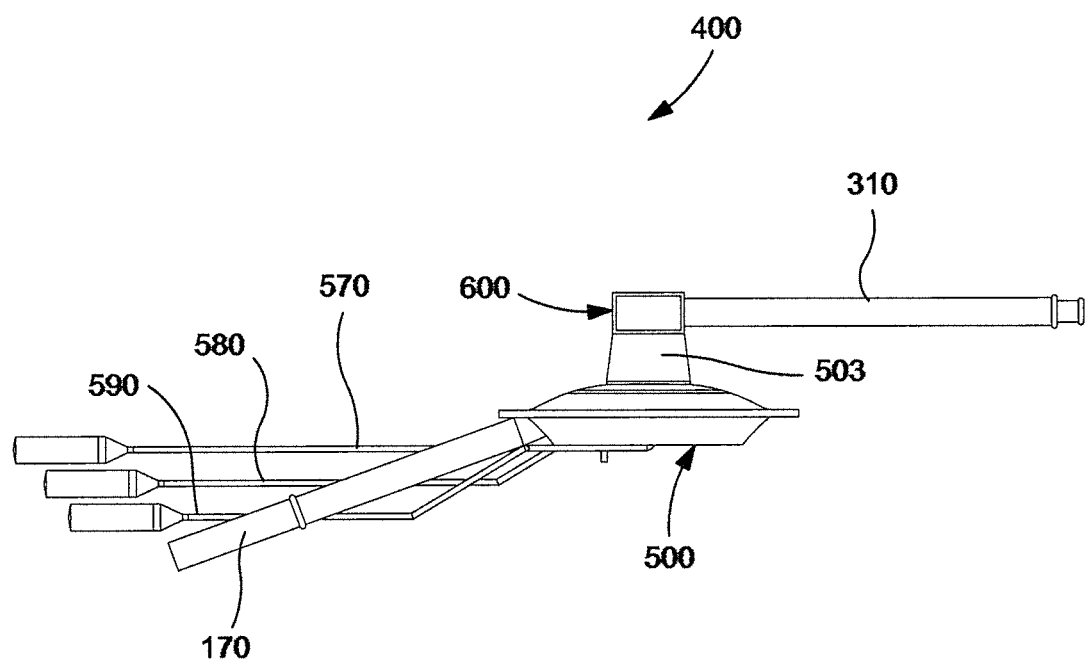
FIG. 4A illustrates Applicants' skin interface device ("SID") 400 comprising an implantable base 500 and a SID cap 600.

Referring now to FIG. 4A, Applicants' SID 400 comprises a SID base 500 and a SID cap 600. SID base 500 and SID cap 600 are coupled so as to create an air-tight conduit between the pneumatic drive line 170 and external air line 310. In this way, pneumatic drive line 170, SID 400, and external air line 310, can be part of a closed fluid system. In certain embodiments, an air-tight seal is formed using gaskets and other sealing systems.

Referring now to FIGS. 4A and 4B, when implanted Applicants' skin interface device 400 includes a SID base 500, comprising a subcutaneous portion 430 internal to the patient, in combination a supracutaneous portion 420. SID cap 600 is attached to the supracutaneous portion 420 of SID base 500. Those skilled in the art will appreciate that it is possible to implant SID 400 in a variety of different locations on the patient, for example abdominally or thoracically.

Figure 4C:
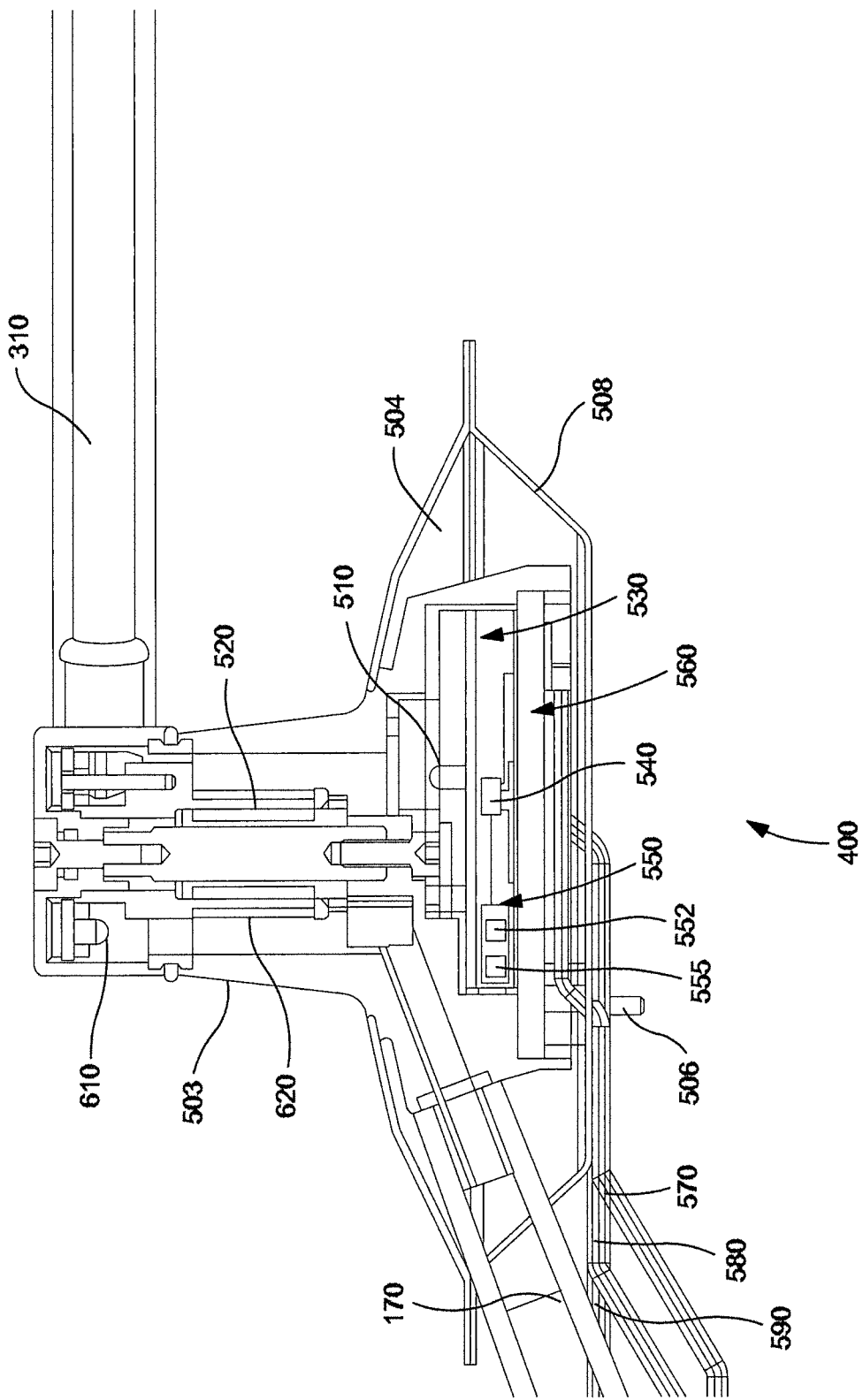
FIG. 4C is a cross-sectional view of Applicants' SID 400 illustrating various components and sub-assemblies.

Referring now to FIGS. 4A and 4C, Applicants' SID 400 wirelessly provides electrical energy from SID cap 600 to SID base 500, and also wirelessly and bi-directionally passes electrical signals, i.e., data, between SID cap 600 and SID base 500. In order to optimize the transmission of power from SID cap 600 to SID base 500, and at the same time optimize the transmission of data between SID cap 600 and SID base 500, Applicants have "decoupled" the transmission of power from the transmission of data. The transmission of power from SID cap 600 to SID base 500 is done by induction.

Figure 6A:
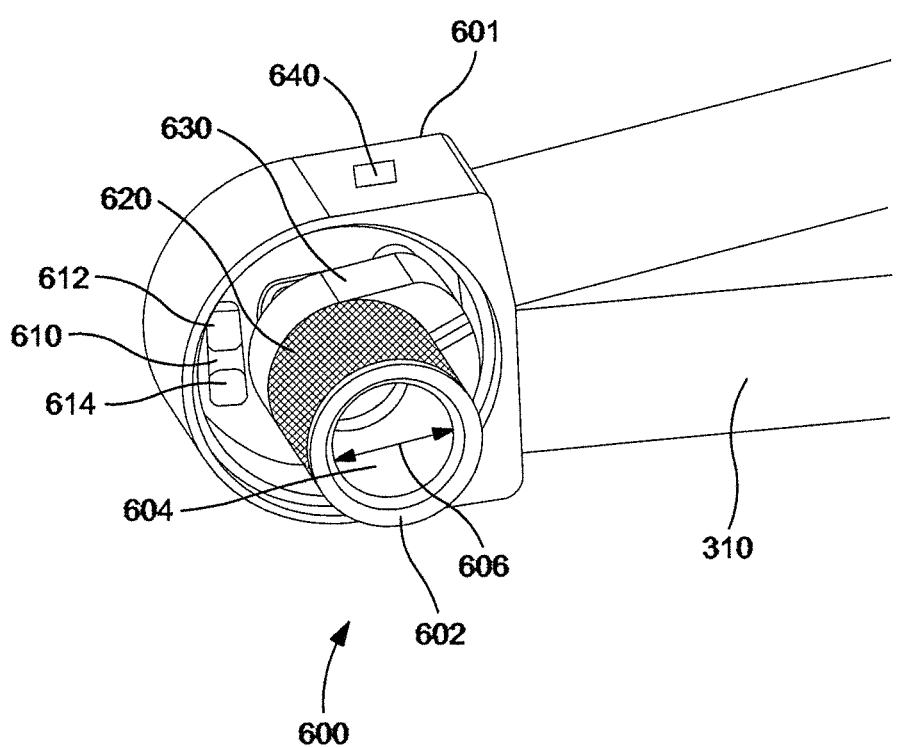
FIG. 6A illustrates SID cap 600 of Applicants' SID 400.

Applicants' SID 400 includes a transformer comprising a primary winding 620 disposed in SID cap 600 and a secondary winding 520 disposed in SID base 500. The SID transformer is configured to power Applicants' SID 400 via an external power source, such as a battery, or conventional 120V or 220V alternating current. During operation of the device the SID transformer transfers power from the external power source to the patient. Importantly, however, the patient is not directly wired to the external power source and is therefore not directly connected to the external power source. Referring now to FIG. 6A, SID cap 600 comprises an annular sleeve 602 attached to and extending outwardly from housing 601. Annular sleeve 602 defines an interior bore 604 having a diameter 606. Primary winding 620 is disposed around the exterior surface of annular sleeve 602.

Figure 5A:
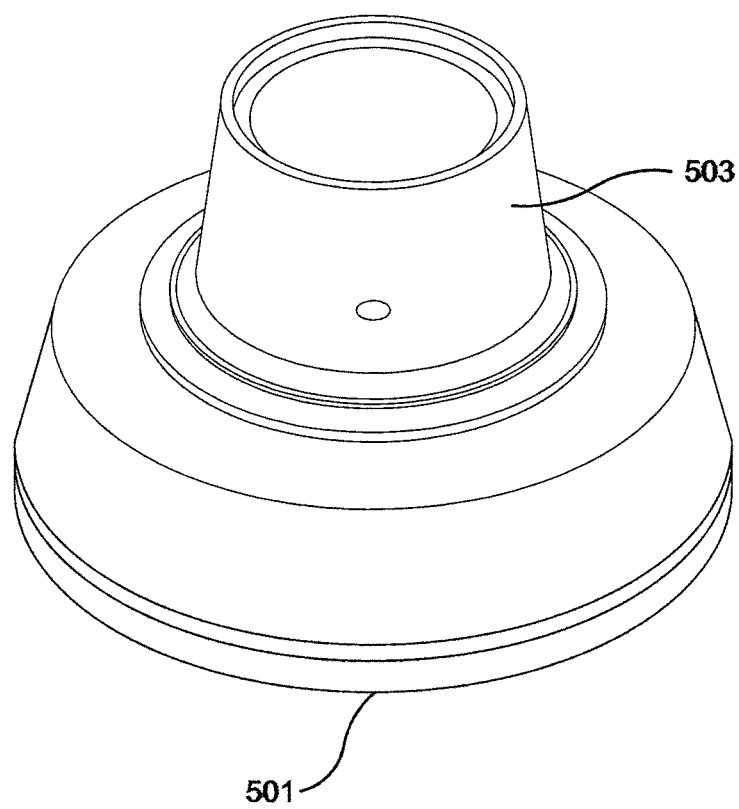
FIG. 5A is a top perspective view of a housing portion of SID base 500.
Figure 5B:
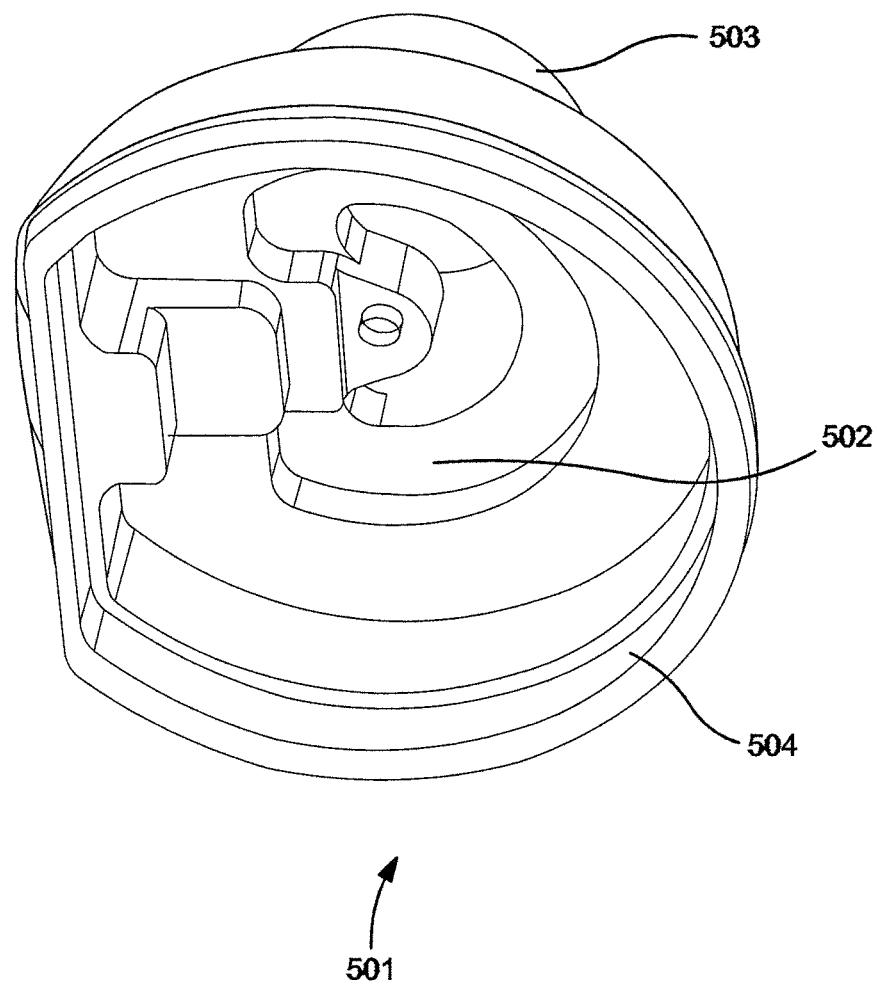
FIG. 5B is a bottom perspective view of the housing portion of FIG. 5A.
Figure 5C:
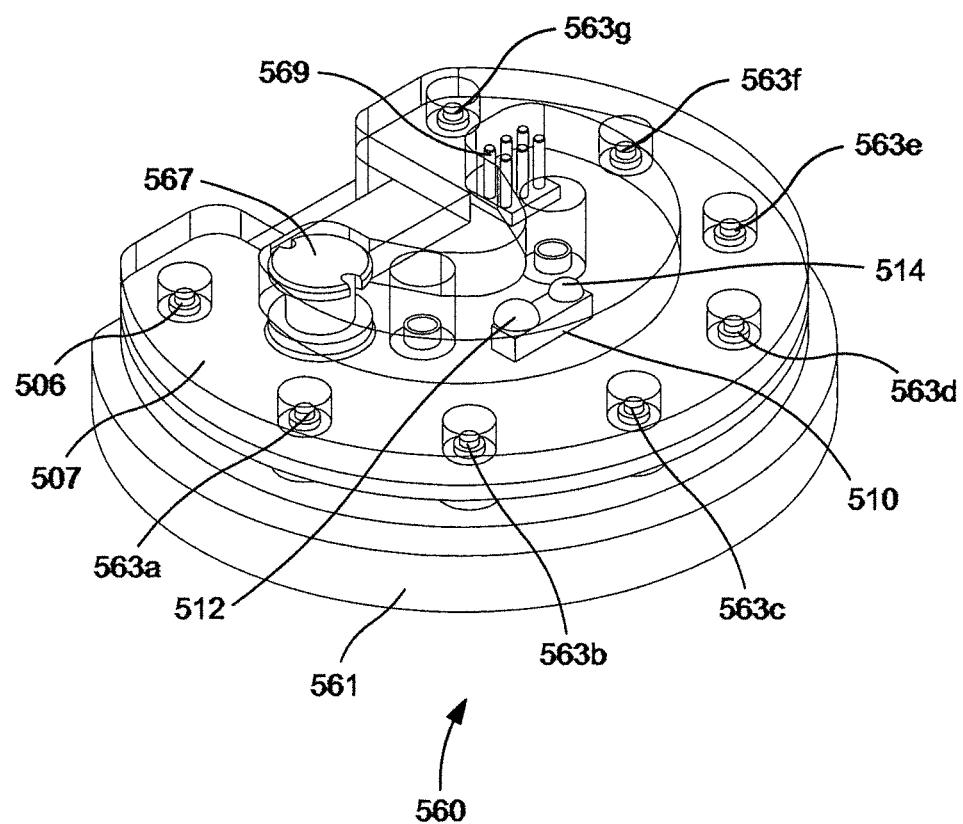
FIG. 5C illustrates various components disposed on an interior surface of a bottom portion 560 of SID base 500.
Figure 5D:
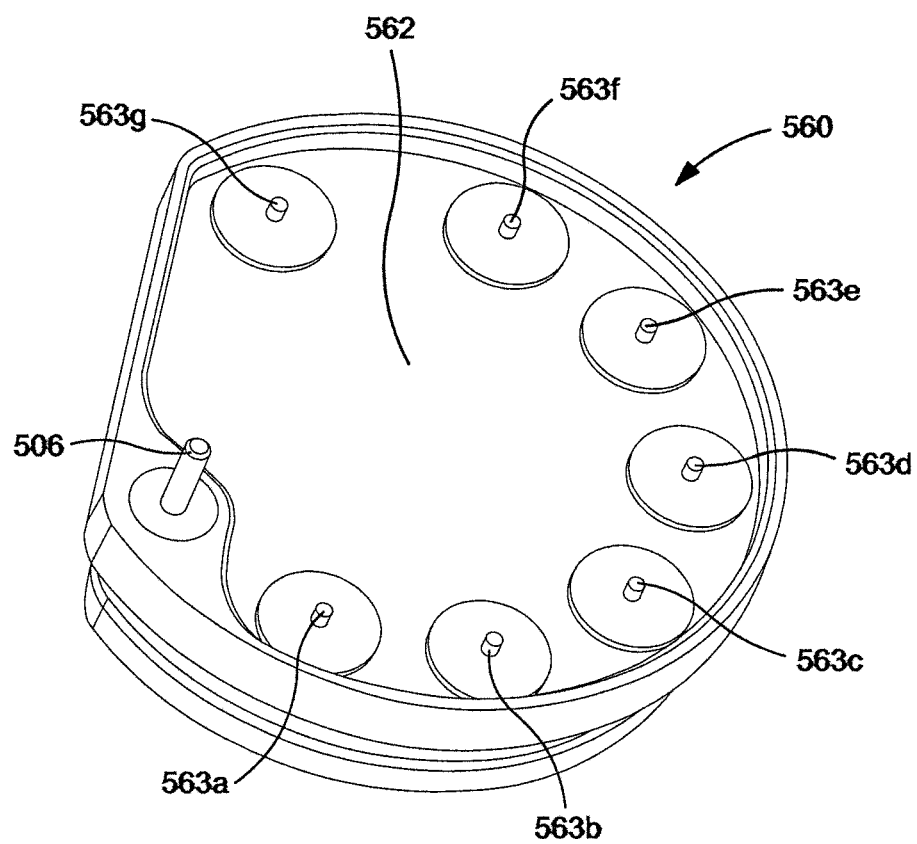
FIG. 5D illustrates various components disposed on an exterior surface of bottom portion 560.
Figure 5E:
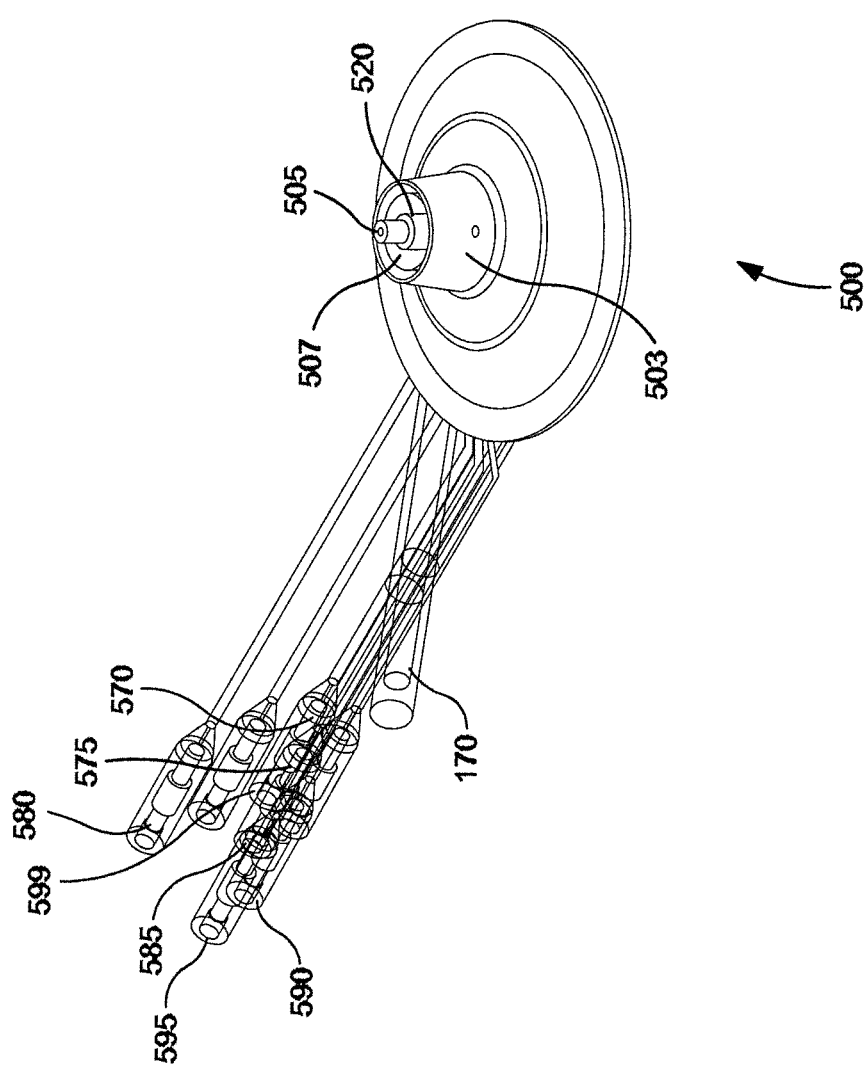
FIG. 5E illustrates a secondary winding portion of a wireless power transfer assembly disposed in SID base 500, in combination with three connectors for EKG sensors, and four connectors for an embedded pressure sensor, attached to Applicants' SID base 500.

Referring to FIG. 5E, cylindrical member 505 is disposed within a bore 507 formed in tubular portion 503. Secondary winding 520 is disposed around cylindrical member 507. FIG. 5E further illustrates seven (7) connectors 570, 575, 580, 585,590, 595, and 599, attached to and extending outwardly from SID base 500. In certain embodiments, three (3) of these connectors may be used to attach three (3) EKG sensors to Applicants' SID 400. In certain embodiments, four (4) of these connectors may be used to attach sensor leads from an implants pressure sensor to Applicants' SID 400.

Figure 6B:
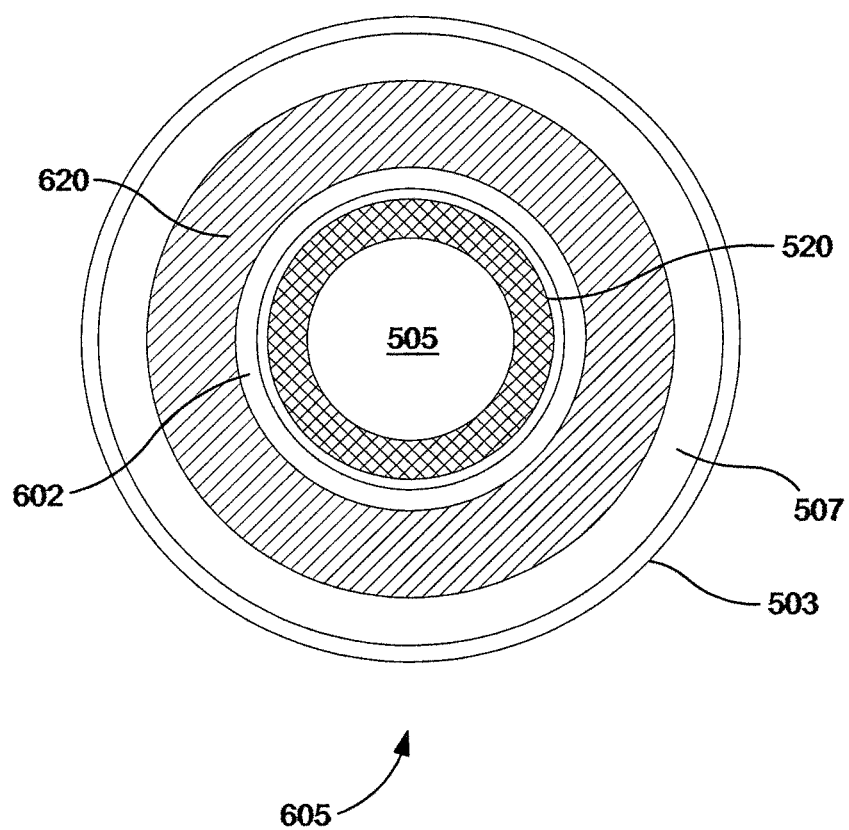
FIG. 6B is a cross-sectional view illustrating various elements of Applicants' wireless power transfer assembly.

FIG. 6B shows a cross-sectional view of wireless power transfer assembly 605, which is formed when SID cap 600 is rotationally attached to tubular portion 503 of SID base 500. Referring now to FIG. 6B, annular secondary winding 520 is disposed around cylindrical member 505. Primary winding 620 is disposed around annular sleeve 602. Primary winding 620/annular sleeve 602 are shown disposed within bore 507 and around secondary winding/cylindrical member 505.

SID cap 600 is configured to be disposed over, and rotationally attached to tubular portion 503 of SID base 500, to form wireless power transfer assembly 605. After such attachment, the relative positions of primary winding 620 and secondary winding 520 are fixed both laterally and vertically. A rotation of SID cap 600 about SID base 500 cannot alter the electrical/magnetic coupling of primary winding 620 and secondary winding 520.

In embodiments, SID cap 600 and tubular portion 503 of SID base 500 are fixed to one another so that they remain attached to each other but are rotatable with respect to one another once initially connected to one another. In this way, SID base 500 can remain stationary with respect to the patient while SID cap 600 can be rotated to accommodate any convenient orientation of the external drive line 310 and any external electrical line. Such rotational decoupling can help reduce or prevent tugging or other stress on the patient's skin or other organs.

In certain embodiments, primary winding 620 comprises Np turns and secondary winding 520 comprises Ns turns. In certain embodiments, Np is substantially equal to Ns. In these embodiments, when first electrical power having a voltage Vp is passed through primary winding 620, a second electrical power having a voltage Vs is induced in secondary winding 520, wherein Vp substantially equals Vs. By "substantially equals," Applicants mean within about plus or minus ten percent (10%).

In certain embodiments, Np is less than Ns. In these embodiments, wireless power transfer assembly 605 comprises a "step up" transformer wherein Vs is greater than Vp. In certain embodiments, Np is greater than Ns. In these embodiments, wireless power transfer assembly 605 comprises a "step down" transformer wherein Vs is less than Vp.

In certain embodiments, annular sleeve 602 is formed from a material comprising a relative magnetic permeability greater than 1. In certain embodiments, annular sleeve 602 is formed from a ferrite. As those skilled in the art will appreciate, ferrites are ceramic materials with iron(III) oxide ($Fe_2O_3$) as a principal component. In certain embodiments, annular sleeve is formed from one or more "soft ferrites." In certain embodiments, annular sleeve comprises nickel, zinc, and/or manganese moieties. In these embodiments, annular sleeve 602 comprises a low coercivity and the annular sleeve's magnetization can easily reverse direction without dissipating much energy (hysteresis losses), while the material's high resistivity prevents eddy currents in the core.

Those skilled in the art will appreciate, that the size of a transformer decreases as the frequency of power passed through the primary winding increases. Use of a soft ferrite facilitates the use of higher frequencies.

In certain embodiments Applicants' SID 400 utilizes a wireless power transfer assembly 605 comprising a polyetheretherketone ("PEEK") core. In certain embodiments Applicants' SID 400 utilizes a wireless power transfer assembly 605 comprising a polyetherimide core.

In certain embodiments, the use of a soft ferrite moieties and frequencies between about 100 kHz and about 1 MHz, in combination with the invariant vertical and lateral alignment of the primary winding 620 and the secondary winding 520, maximizes the efficiency of wireless power transmission within SID 400.

Power that is not effectively transmitted from the SID cap 600 to the SID base 500 is lost as heat. SID 400 is an implantable device and is intended for long-term use in a patient. It is known that at temperatures in the range of about 41° C. to about 43° C., damage to adjacent tissues can begin. It is further known that at temperatures greater than about 43° C., surrounding tissues will be damaged.

Needless to say, tissue damage in near vicinity to an implanted medical device can be a source of infection. The optimized efficiency of power transmission within Applicants' implantable SID 400 allows the use of more power within that device without increasing a likelihood of infection.

Applicants' SID 400 further comprises a pair of infrared transceiver assemblies to bi-directionally wirelessly transmit data between SID cap 600 and SID base 500. Referring to FIG. 4C, SID cap 600 comprises a first infrared data transceiver assembly 610. SID base 500 comprises a second infrared transceiver assembly 510.

In certain embodiments, infrared transceiver assemblies 510 and 610 each comprise at least one infrared diode and signal processing circuitry. In certain embodiments, infrared transceiver assemblies 510 and 610 each utilize one or more infrared diodes emitting infrared energy at wavelengths between about 780 nm to about 1550 nm.

In certain embodiments, the infrared diode and processing circuitry are efficient enough to fit into a small module whose transceiver has the dimensions of a child's fingernail. In certain embodiments, infrared transceiver assemblies 510 and 610, are capable of exchanging data at a rate of about 1 Gbps.

Referring to FIG. 5C, infrared transceiver assembly 510 disposed in SID base 500 comprises infrared diode 512 and infrared diode 514. Referring to FIG. 6A, infrared transceiver assembly 610 disposed in SID cap 600 comprises infrared diode 612 and infrared diode 614.

Referring once again to FIG. 4C, in certain embodiments Applicants' SID 400 comprises controller 530. Controller 530 comprises processor 540 and non-transitory computer readable medium 550. In certain embodiments, computer readable medium 550 comprises a non-volatile memory device, such as and without limitation battery-backed up RAM; an electronic storage medium; a hard disk drive assembly comprising a magnetic disk storage medium and ancillary hardware, software, and firmware needed to write data to, and read data from, the magnetic disk; an optical disk drive assembly comprising a rewriteable optical disk and ancillary hardware, software, and firmware needed to write data to, and read data from, the optical disk.

In certain embodiments, computer readable medium 550 comprises a rewritable memory device, such as and without limitation an EEPROM or NAND flash memory.

In certain embodiments, patient data 552 is encoded in computer readable medium 550. In certain embodiments, patient data 552 comprises timing data related to the inflation and deflation of the pump 180. When a patient changes drive units 320, the new drive unit reads the timing data from Applicants' SID 400 and adjusts its timing parameters accordingly.

In certain embodiments, computer readable medium 550 is configured to store data; e.g., in primary or secondary memory storage module, accumulated during operation of Applicants' SID 400, or information obtained during a doctor's visit. The information may be accessed either by a doctor, for example to investigate the past performance of Applicants' SID 400, or to obtain data on the patient's health as detected by sensors used to collect data during operation. Or the information may be accessed by processor 540, for example to set parameters for operation of Applicants' SID 400.

In certain embodiments, computer readable medium 550 is configured to store various types of data accumulated during operation of Applicants' SID 400. For example, data obtained from sensors by be stored in a memory storage module to assess a patients well being, such as EKG signals, pulse, body temperature, blood pressure, blood analytes and the like, all which may be measured and stored as a function of time. Additionally, data may be stored to assess performance of Applicants' SID 400 during operation. For example data pertaining to operational parameters of components of Applicants' SID 400 may be stored, such as drive unit 320 usage, including timing and volume of pumping, as well as errors in component operation or function. In this manner component usage logs may be compiled and stored on computer readable medium 550. Similarly, event logs may be compiled and stored on computer readable medium 550. As discussed above, the information may be accessed either by a doctor, for example to investigate the past performance of Applicants' SID 400 or to obtain data on the patient's health. Or the information may be accessed by processor 540, for example to set parameters for operation of Applicants' SID 400.

Computer readable program code 555 is encoded in computer readable medium 550. Processor 540 is in bi-directional communication with computer readable medium 555. Processor 540 utilizes computer readable program code 555 to operate Applicants' SID 400.

In certain embodiments, processor 540, computer readable medium 550, and computer readable program code 555, are integrated in an Application Specific Integrated Circuit.

In certain embodiments, Applicants' SID base 500 further comprises a fabric cover 508 disposed over the exterior surface of SID base 500. In certain embodiments fabric cover 508 is formed to include a plurality of pores extending therethrough. In certain embodiments, fabric cover 508 comprises a polymeric material such as ePTFE of pore size 10-100 microns. In certain embodiments, fabric cover 508 is formed to include pores having a diameter of between about 30 to about 60 microns. The plurality of pores formed in fabric 508 comprise a diameter sufficient to allow cells to form attachments thereto.

Referring to FIG. 5A, in certain embodiments housing 501 for SID base 500 is machined from a block of titanium. Housing 501 is formed to include central tubular portion 503. FIG. 5B illustrates an interior bore 502 formed in housing 501, wherein interior bore is in fluid communication with tubular portion 503.

Referring now to FIGS. 5C and 5D, assembly 560 comprises a bottom portion of SID base 500. Flange 561 of assembly 560 can be attached to bottom lip 504 of housing 501 to form a substantial portion of the exterior of SID base 500.

FIG. 5D illustrates a bottom surface 562 of assembly 560. A distal end of platinum/iridium electrode 506 extends outwardly from surface 562. In certain embodiments, platinum/iridium electrode 506 is interconnected with controller 530, wherein controller 530 utilizes platinum/iridium electrode 506 as an electrical reference.

Distal ends of connecting members 563*a*, 563*b*, 563*c*, 563*d*, 563*c*, 563*f*, and 563*g*, extend outwardly from surface 562. Referring to FIGS. 5D and 5E, in certain embodiments three (3) connecting members, such as and without limitation connecting members 563*a*, 563*b*, and 563*c*, can be used to electrically attach three EKG sensors to SID base 500. In certain embodiments, four (4) connecting members, such as and without limitation connecting members 563*d*, 563*e*, 563*f*, and 563*g*, can be used to electrically attach pressure sensor leads 192, 194, 196, and 198, to SID base 500.

Referring again to FIG. 5C, the platinum/iridium electrode 506, and connecting members 563*a*, 563*b*, 563*c*, 563*d*, 563*e*, 563*f*, and 563*g*, extend through flange portion 561 of assembly 560, and into circuitry layer 507. In certain embodiments, the platinum/iridium electrode 506, and connecting members 563*a*, 563*b*, 563*c*, 563*d*, 563*e*, 563*f*, and 563*g*, are interconnected to processor 540.

In certain embodiments, the elements of controller 530 are disposed within circuitry layer 507. In other embodiments, controller 530 is disposed on top of circuitry layer 507. In certain embodiments, infrared transceiver assembly 510 is disposed on top of circuitry layer 507. In the illustrated embodiment of FIG. 5C, infrared transceiver assembly 510 comprises infrared diode 512 and infrared diode 514. Infrared transceiver assembly 510 is interconnected with processor 540.

In certain embodiments, circuitry layer 507 comprises a rectifier section and/or an output power filtering section. In these embodiments, such a rectifier section and/or such a power filtering section is interconnected with secondary winding 520.

In the illustrated embodiment of FIG. 5C, device 567 is disposed on top of circuitry layer 507. In the illustrated embodiment of FIG. 5C, connector assembly 569 is disposed in top of circuitry layer 507.

Figure 9:
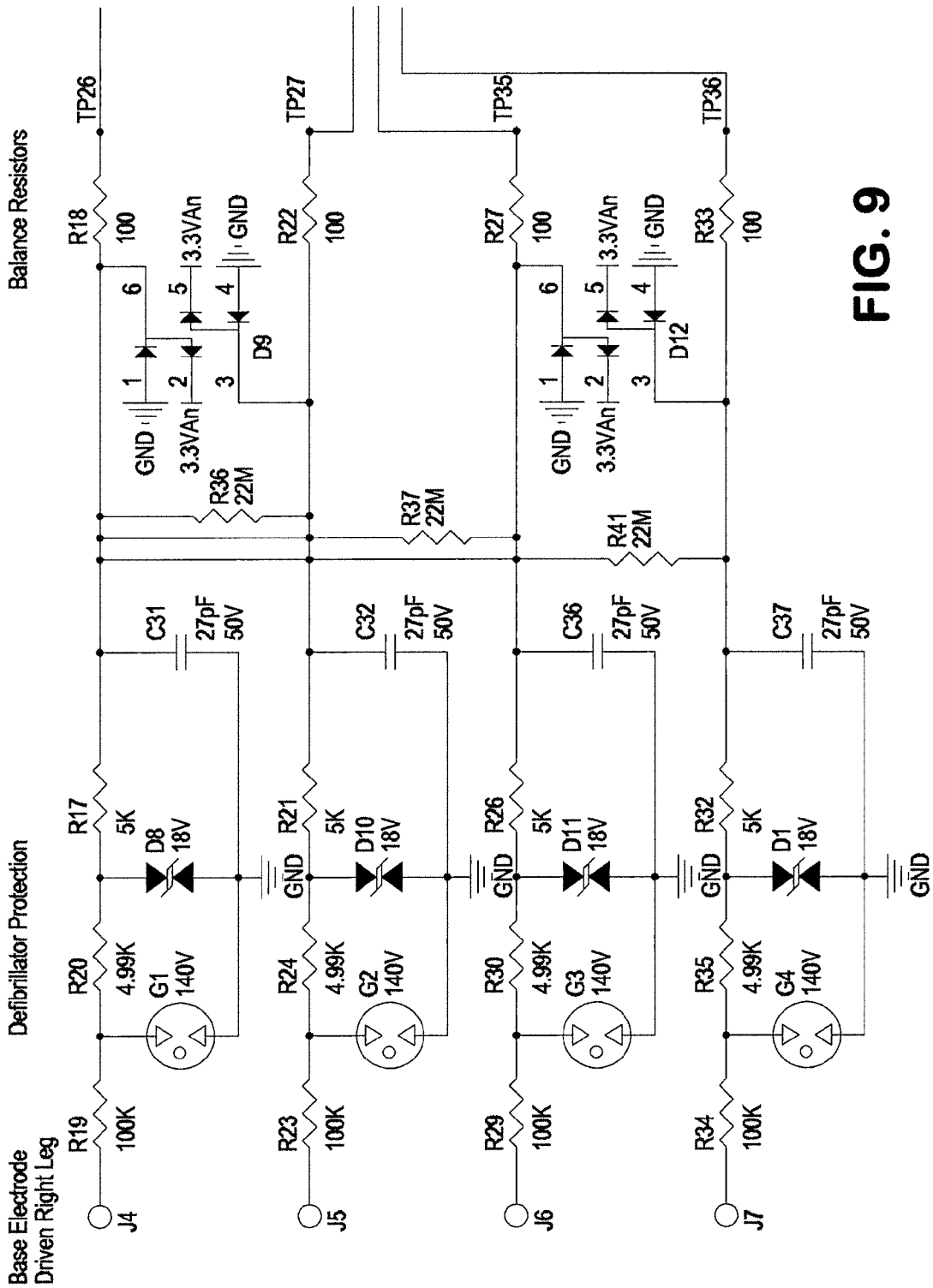
FIG. 9 is a schematic showing circuitry for clamping down externally administered high voltage shocks (signals).

A key aspect of the Applicants' SID 400 is that it provided with circuitry that allows the device to withstanding an externally applied electrical shock from a conventional defibrillation device (about 5000V) while still being able to detect, process and store low power signals, such as those from an EKG sensor. SID 400 includes passive circuitry which functions to "clamp" down a high voltage shock which is administered to a patient who is wearing the device but required defibrillation. One embodiment of the circuitry operable to clamp down externally applied voltages of greater than 5000V is shown in FIG. 9. This feature ensures that the device is not rendered nonoperational which could pose great harm to the patient. Advantageously, however, patients undergoing cardiac support through use of the device according to the invention can be expected to continue functioning at no lower than baseline (cardiac function prior to device operation) and potentially at a higher level of function, without risk of advsere cardiac effects (see, e.g., Kantrowitz, et al., *ASAIO Journal*, 41(3): M340-M345 (1995) (no histological damage following in vivo operation and deactivation of a ventricle assist device in cows); Li, et al., *ASAIO Journal*, 46(2): 205 (2000) (no ill effects from deactivation then reactivation after two months); and, Jeevanandam, et al., *Circulation*, 106:1-183-1-188 (2002) (cardiac evaluation in humans implanted with a permanent ventricle assist device)).

Referring once again to FIG. 6A, SID cap 600 comprises housing 601, infrared transceiver assembly 610, and annular sleeve 602/primary winding 620 extending outwardly from housing 601.

Referring to FIG. 6A, SID cap 600 may additionally include one or more access ports for both electrical signals and fluid lines (not shown). For example, SID cap 600 may have additional access ports for fluid communication with more than one external drive line, such as multiple drive lines 310. Similarly, SID cap 600 may include one or more access ports for external electrical lines. For example, one or more access ports may be provided such that the SID may be connected to external electrical line for connection to an external processor or memory. In this manner data may be transferred from computer readable medium 555 to an external processor. The access port may also be configured to receive data from an external processor.

Power supplied to SID cap 600 is provided to primary winding 620, which wirelessly provides power to SID base 500 via secondary winding 520. In certain embodiments, controller 530 receives power from secondary winding 520. In certain embodiments, SID base 500 comprises one or more rechargeable batteries, wherein those one or more rechargeable batteries receive power from secondary winding 520.

In certain embodiments, SID cap 600 further comprises communication port 640. In certain embodiments, communication port 640 comprises a USB port.

In certain embodiments, communication port 640 comprises an IEEE 1394 interface, i.e., a "firewire" port. In certain embodiments, communication port 640 is in communication with controller 530 via infrared transceivers 510 and 610.

In certain embodiments, SID cap 600 further comprises a wireless communication module 630 configured to communicate wirelessly with one or more computing devices external to SID 400. In certain embodiments, wireless communication module 630 is in communication with controller 530 via infrared transceivers 510 (FIGS. 4C, 5C) and 610 (FIGS. 4C, 6A).

In certain embodiments, wireless communication module 630 utilizes "WI FI" technology in accord with the IEEE 802.11 Standard. As those skilled in the art will appreciate, the 802.11 family consist of a series of half-duplex over-the-air modulation techniques that use the same basic protocol. Standard 802.11n is a new multi-streaming modulation technique. Other standards in the family (c-f, h, j) are service amendments and extensions or corrections to the previous specifications.

In certain embodiments, wireless communication module 630 utilizes "Bluetooth" technology. As those skilled in the art will appreciate, Bluetooth is a wireless technology standard for exchanging data over short distances (using short-wavelength radio transmissions in the ISM band from 2400-2480 MHz) from fixed and mobile devices, creating personal area networks (PANs) with high levels of security.

In certain embodiments, controller 530 can provide data to one or more computing devices external to Applicants' SID 400. In certain embodiments, controller utilizes wireless communication module 630. In certain embodiments, controller 530 utilizes a wired interconnection with the one or more external computing devices utilizing communication port 640.

In certain embodiments, three (3) EKG sensors provide signals to controller 530. In certain embodiments, controller 530 utilizes computer readable program code 555 to analyze the signals from the three interconnected EKG sensors to detect a QRS complex.

In certain embodiments, controller 530 evaluates the signals from three (3) EKG sensors. In certain embodiments, controller 530 utilizes combinations of signals from three (3) EKG sensors. In certain embodiments, controller 530 evaluates signals from three (3) EKG sensors with reference to certain nominal signal characteristics encoded in computer readable program code 555. In certain embodiments, controller 530 rejects signals received from one or more interconnected EKG sensors, where signals from those one or more EKG sensors do not meet the encoded nominal signal characteristics.

In certain embodiments, SID 400 includes computer readable program code 555 encoded in non-transitory computer readable medium 550, where computer readable program code 555 is executed by processor 540 to receive signals from one or more implanted EKG sensors, evaluate the signals received from one or more implanted EKG sensors with reference to certain nominal signal characteristics encoded in computer readable program code 555, reject signals received from one or more interconnected EKG sensors if signals from those one or more EKG sensors do not meet the encoded nominal signal characteristics, and store in the non-transitory computer readable medium 550 signals that do meet the encoded nominal signal characteristics.

In certain embodiments, SID 400 includes computer readable program code 555 encoded in non-transitory computer readable medium 550, where computer readable program code 555 is executed by processor 540 to receive a plurality of signals from EKG sensors, to optionally utilizes combinations of signals from the plurality of EKG sensors, and to analyze the signals from the plurality of EKG sensors to detect a QRS complex.

Figure 7:
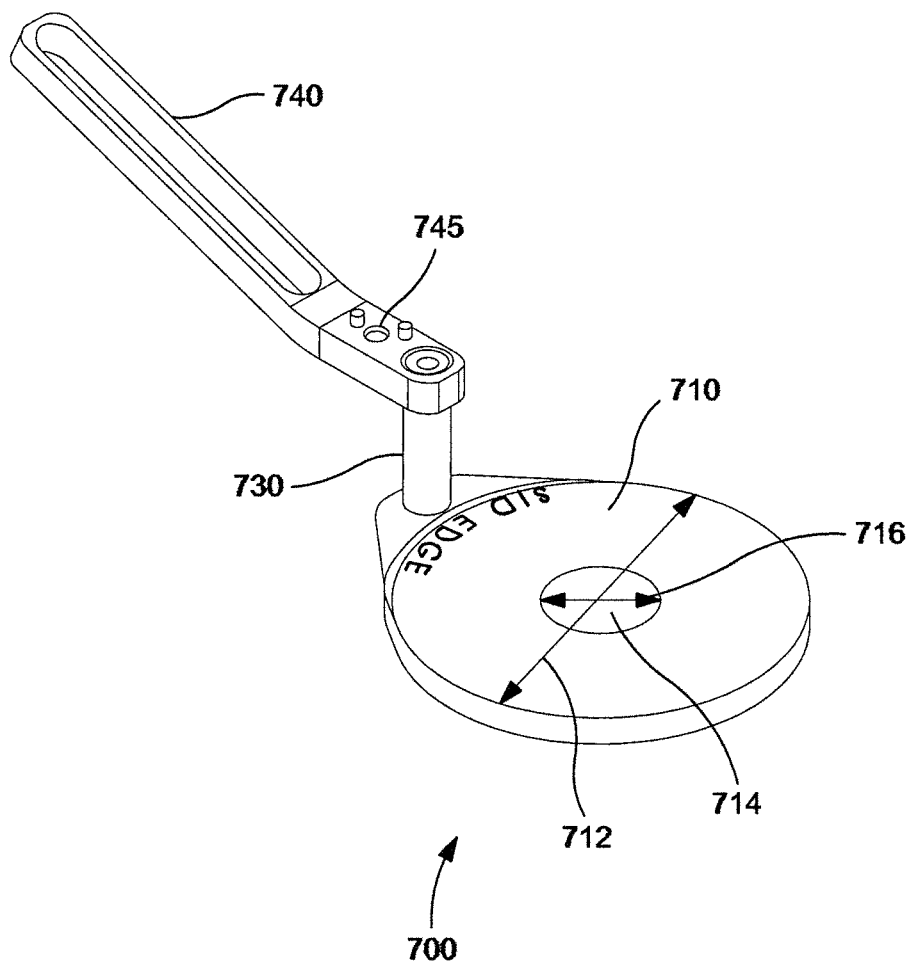
FIG. 7 is a perspective view of a handle and base portion 700 of Applicants' trephine surgical instrument 800 used to subcutaneously position Applicants' SID 400 within a patient.
Figure 8A:
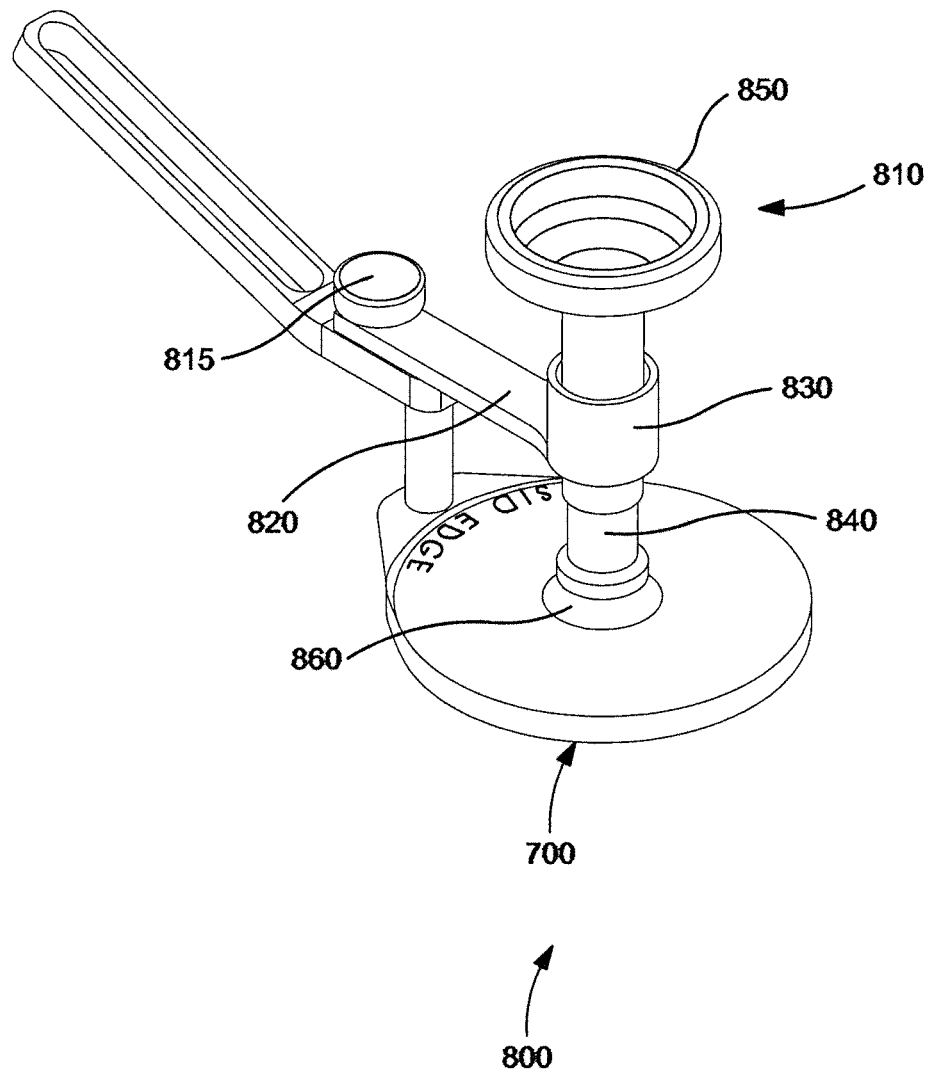
FIG. 8A is a perspective view of Applicants' trephine surgical instrument 800 used to subcutaneously implant Applicants' SID 400 within a patient.

Referring now to FIGS. 7 and 8A, Applicants' SID 400 can be implanted into a patient using Applicants' trephine surgical instrument 800. Trephine surgical instrument 800 comprises base portion 700 in combination with removeably attachable assembly 810. Referring to FIG. 7, trephine surgical instrument base portion 700 comprises platen 710 having a diameter 712. Platen 710 is formed to include plastic disk 714 having a diameter 716. In certain embodiments, platen diameter 712 is substantially equal to the maximum diameter 420 (FIG. 4A) of SID base 500. In certain embodiments, diameter 716 of plastic disk 714 is substantially equal to maximum diameter 410 (FIG. 4A) of tubular portion 503.

A first end of member 730 is attached to the periphery of platen 710 and extends upwardly therefrom. Handle 740 is attached to a second end of member 730. Handle 740 is formed to include a threaded aperture 745 extending inwardly therein from a top surface.

When preparing to subcutaneously implant Applicants' SID 400, a surgeon can subcutaneously insert trephine platen 710 through an incision in the skin. The surgeon then utilizes platen 710 to form a subcutaneous pocket dimensioned to accept Applicants' SID 400. Applicants have found that subassembly 700 can be more easily manipulated than can full trephine surgical instrument assembly 800 when forming such a subcutaneous pocket.

Figure 8B:
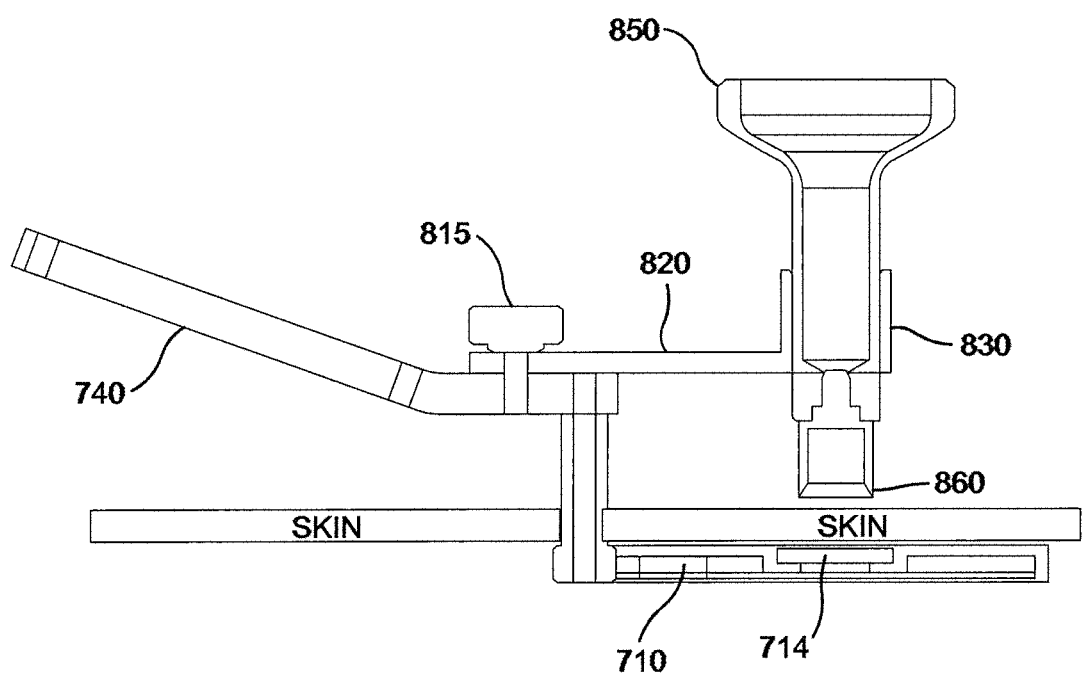
FIG. 8B is a section view of the trephine surgical instrument 800, wherein bottom platen 710 has been used to form a subcutaneous pocket to receive Applicants' SID base 500, and wherein upper assembly 810 is being used to form a circular aperture in the skin through which a tubular portion of SID base 500 can extend outwardly.

Referring now to FIGS. 8A and 8B, after forming a subcutaneous pocket dimensioned to accept SID base 500, the surgeon can attach upper assembly 810 using a securing means 815 inserted through horizontal member 820 and into threaded aperture 745. Upper assembly 810 comprises horizontal member 820 having annular ring 830 disposed on a distal end thereof.

Cylindrical member 840 is slidingly disposed through annular ring 830. A circular handle 850 is disposed on an upper end of cylindrical member 840. An annular blade assembly 860 is disposed on the lower end of cylindrical member 840.

FIG. 8B shows a section view of trephine surgical instrument 800 with platen 710 disposed within a subcutaneous pocket, as described hereinabove. Downward and circular pressure can be applied to circular handle 850 to urge cylindrical member 840 downwardly through annular ring 830 such that annular blade assembly 860 passes through the skin and onto plastic disk 714 thereby forming a circular incision through the skin. In certain embodiments, the diameter of that circular incision is slightly smaller than diameter of tubular portion 503 of SID base 500.

While the preferred embodiments of the present invention have been illustrated in detail, it should be apparent that modifications and adaptations to those embodiments may occur to one skilled in the art without departing from the scope of the present invention as set forth herein. The invention is illustrated in part by the following example; provided however, that the invention is solely defined by the appended claims.

Example I

The following procedures were followed to determine the time required for the drive unit to inflate the blood pump. From the data, two different times were computed. The first time (bellows inflation time) is defined as the length of time required for the bellows to complete its compression stoke. The second time (blood pump inflation time) is defined as the period that elapses while the volume of the blood pump changes from 0 to fully inflated. The test covered the Drive Unit, Inspired Energy battery NH2054HD31 (Vnom=14.4V, 5.8 Ah), Drive Unit Software—LabVIEW version.

The end points for inflation cycle time targets within acceptable parameters were: 1) Maximum inflation time target, 160 msec; 2) Nominal inflation time target, 130 msec; and 3) Minimum inflation time target, 100 msec.

The test protocol followed for a heart rate of 90 BPM and a diastolic pressure of 80 mmHg was:
1. Power Source—chose one of the two options listed below
   a. Battery Power
      i. Charge the internal battery of the drive unit to at least 50%.
      ii. Remove any battery present in the external battery socket of the drive unit.
      iii. Disconnect the DC power brick from the drive unit.
   b. Power Supply
      i. Use a 24V DC supply to power the bellows motor
      ii. Use a 12V DC supply to power the valves
2. Set the ECG signal generator to output a signal of 90 bpm.
3. Set the pressure inside the compliance chamber to 80 mmHg.
4. Turn the dicrotic notch simulation off.
5. Start the drive unit.
6. Allow the drive unit to complete the startup procedure and begin pumping in the closed mode following the ECG signal at a rate of 90 bpm.
7. Record 20 s of data while the drive unit is operating.

Results were recorded as "bellows inflation time—length of time require for the bellows to traverse from its home position to the fully compressed position; "blood pump inflation time"; and, "bellows deflation time—length of time require for the bellows to traverse from its fully compressed position to the home position". If the drive unit traversed from home to fully compressed in ≤160 ms, the test was successful.

Figure 10:
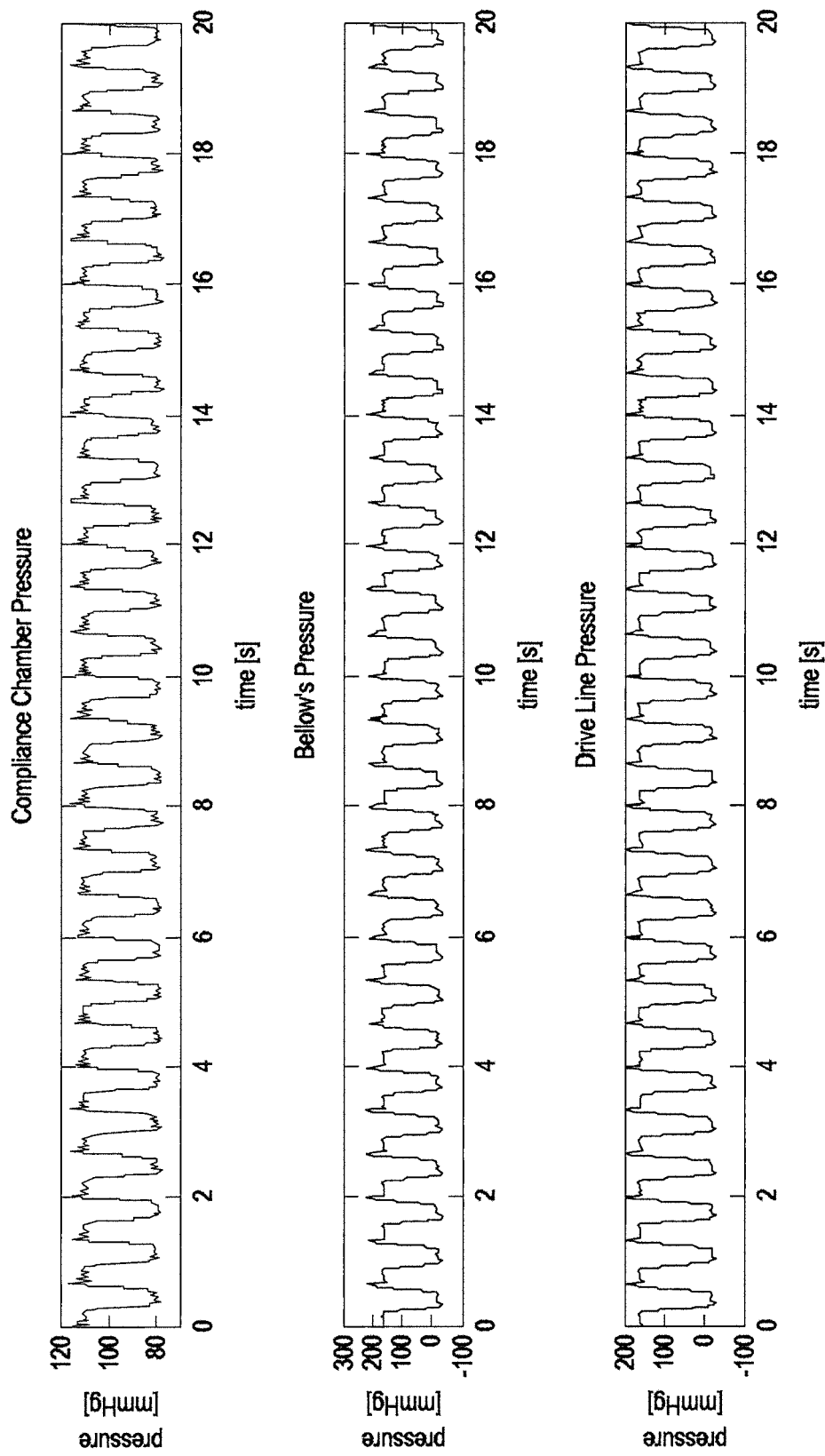
FIG. 10 is a graph showing pressure data generated via one embodiment of the device of the present invention in which the drive unit is operated in closed pumping mode.
Figure 11:
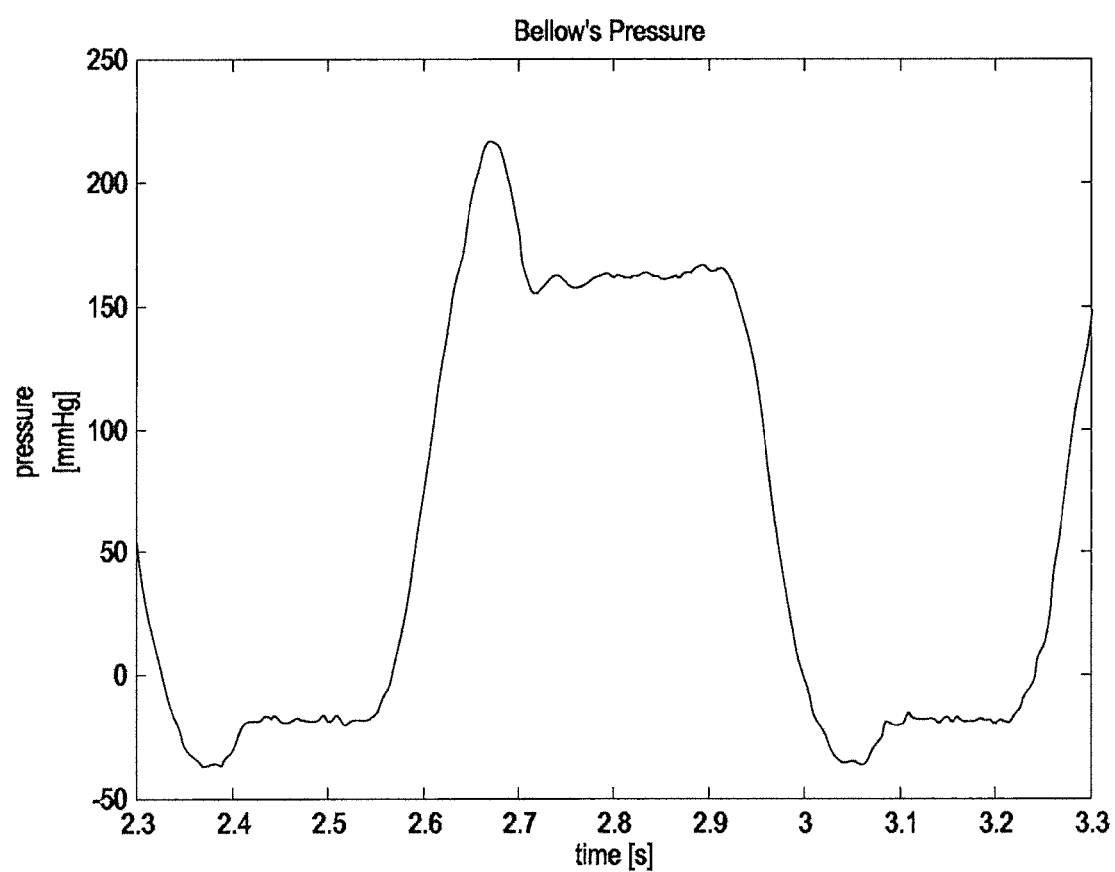
FIG. 11 is a graph showing pressure data generated via one embodiment of the device of the present invention.
Figure 12:
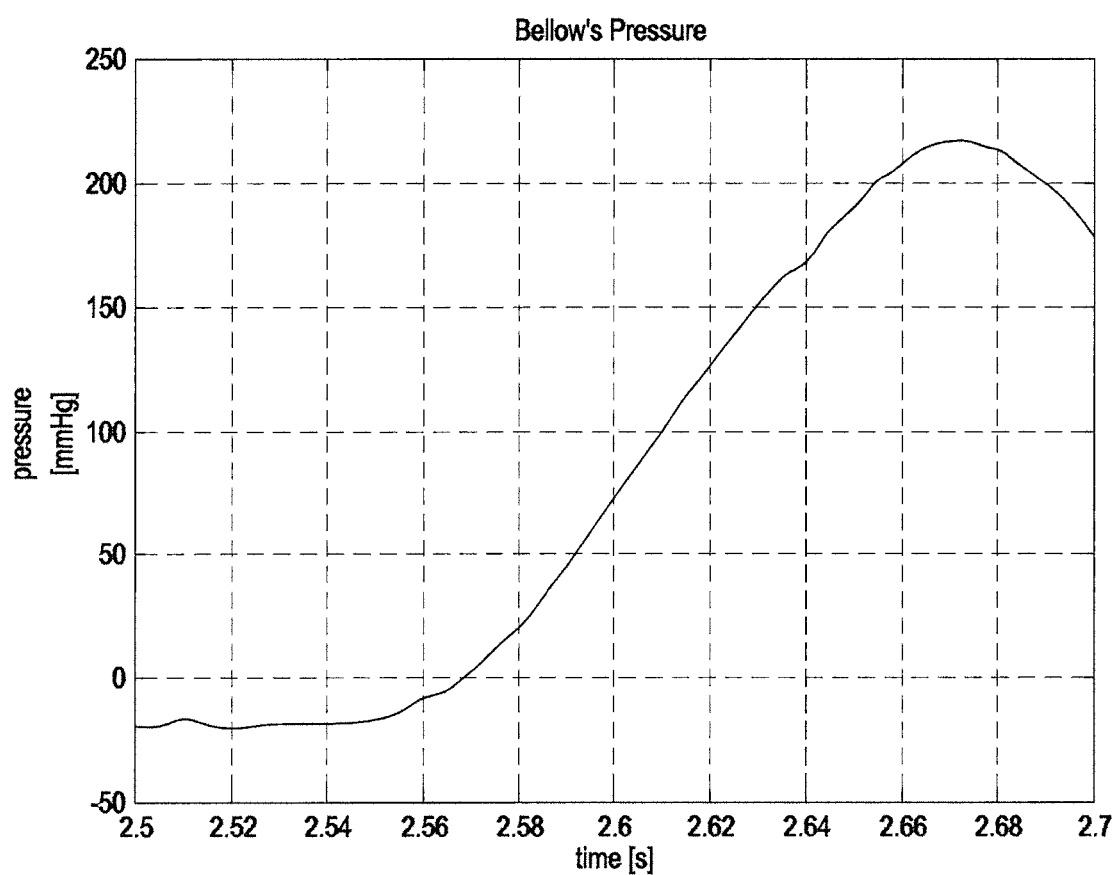
FIG. 12 is a graph showing pressure data generated via one embodiment of the device of the present invention.

FIG. 10 shows pressure data collected while the drive unit was operating in the closed pumping mode. From the compliance chamber data, the diastolic pressure of the experiment was 80 mmHg and the systolic pressure was ~110 mmHg. FIG. 11 displays the bellow's pressure data recorded between 2.3 and 3.3 s of the experiment. FIG. 12 displays the bellow's pressure data recorded between 2.5 and 2.7 s. The process of inflating the blood pump began at 2.55 s when the pressure started to increase. The inflation process ended 2.67 s when the maximum pressure was reached. From this data, the bellows inflation time equaled 120 ms.

The blood pump inflation time can also be determined from FIG. 12. The volume of the blood pump remains zero until the pressure inside the bellows exceeds aortic pressure. From FIG. 12, the bellows pressure did not exceed the diastolic pressure of the compliance chamber until ~2.6 s. Inflation of the blood pump ended at 2.67 s when the maximum pressure was achieved. From this data, the blood pump inflation time equaled 70 ms.

Figure 13:
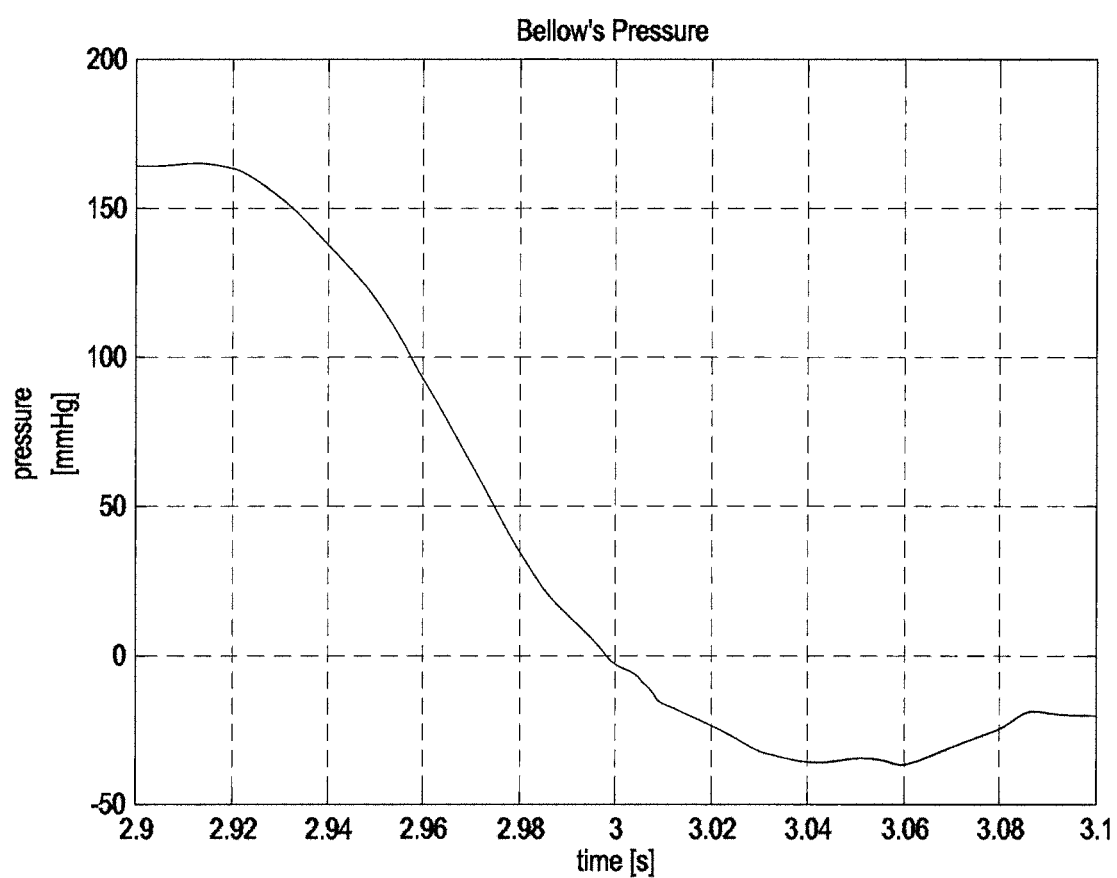
FIG. 13 is a graph showing pressure data generated via one embodiment of the device of the present invention during bellow deflation.

Deflation of the blood pump is shown in FIG. 13 where bellow's pressure data is plotted during the expansion stroke of the bellows. Deflation began at 2.92 s when the pressure started to decrease. Deflation ended at 3.05 s when the pressure reached a minimum. The bellows deflation time equaled 130 ms. Thus, the blood pump was observed to inflate and deflate correctly.

Inflation duration was also measured for a heart rate of 90 BPM and a diastolic pressure of 120 mmHg. The test protocol was generally as described above, with the pressure inside the compliance chamber being set to 120 mmHg. If the drive unit traversed from home to fully compressed in ≤160 ms, the test was successful.

Figure 14:
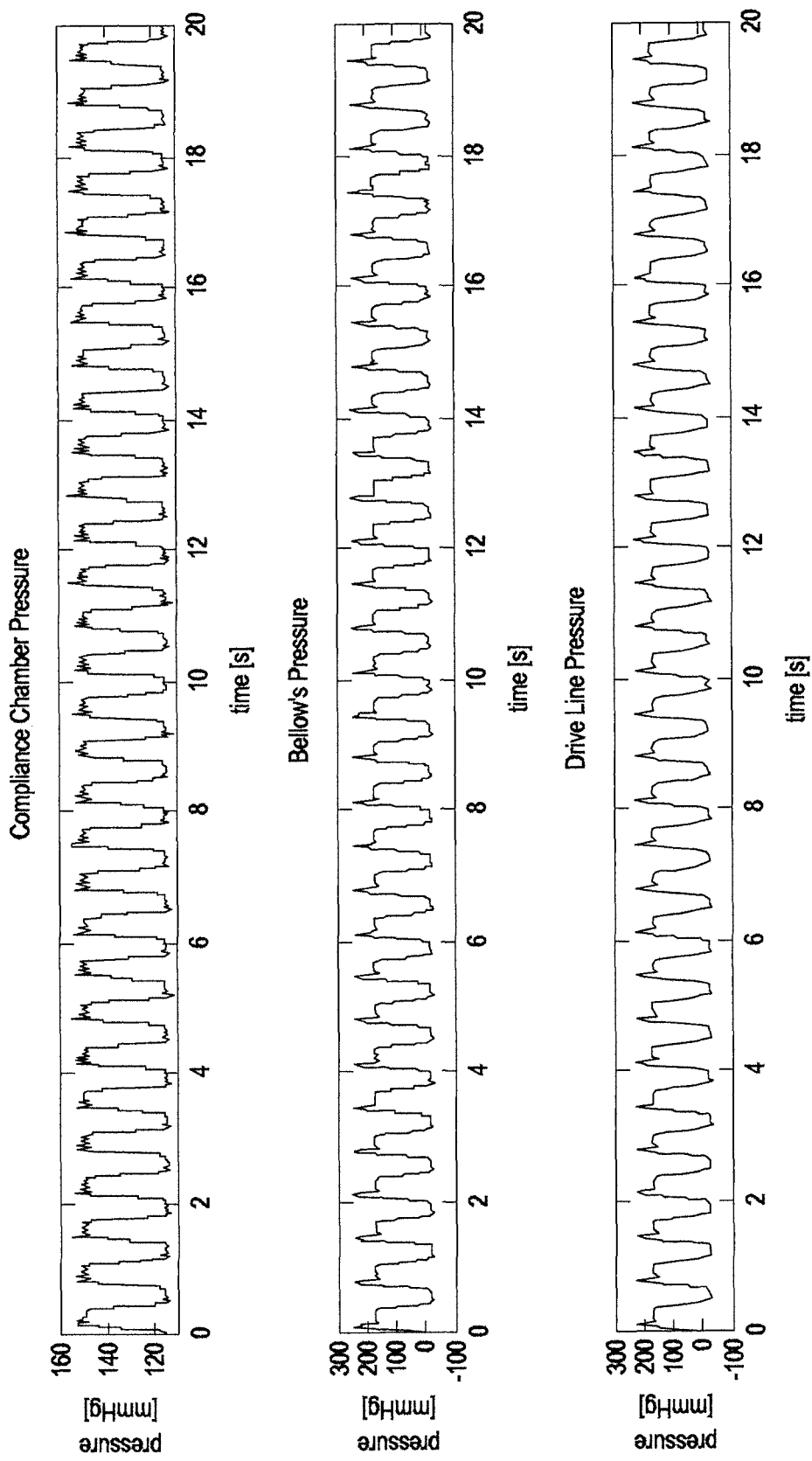
FIG. 14 is a graph showing pressure data generated via one embodiment of the device of the present invention in which the drive unit is operated in closed pumping mode.
Figure 15:
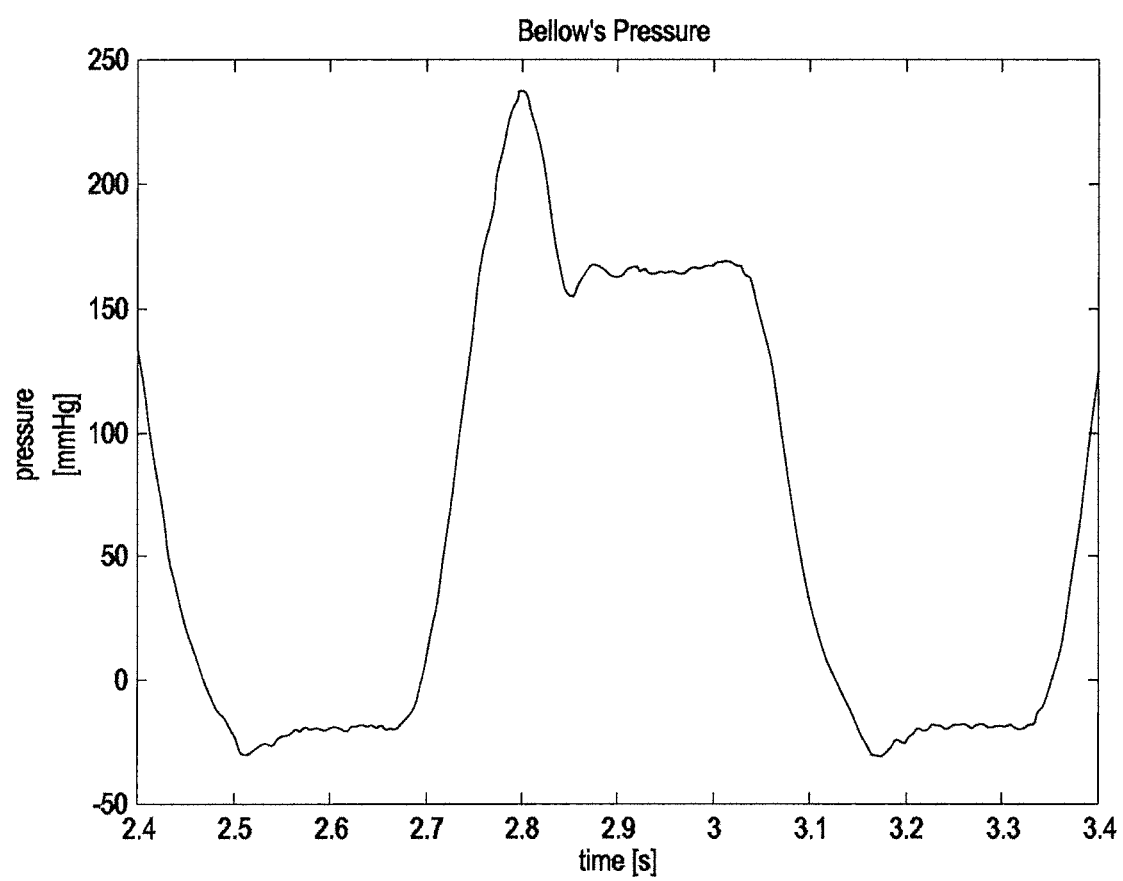
FIG. 15 is a graph showing pressure data generated via one embodiment of the device of the present invention.
Figure 16:
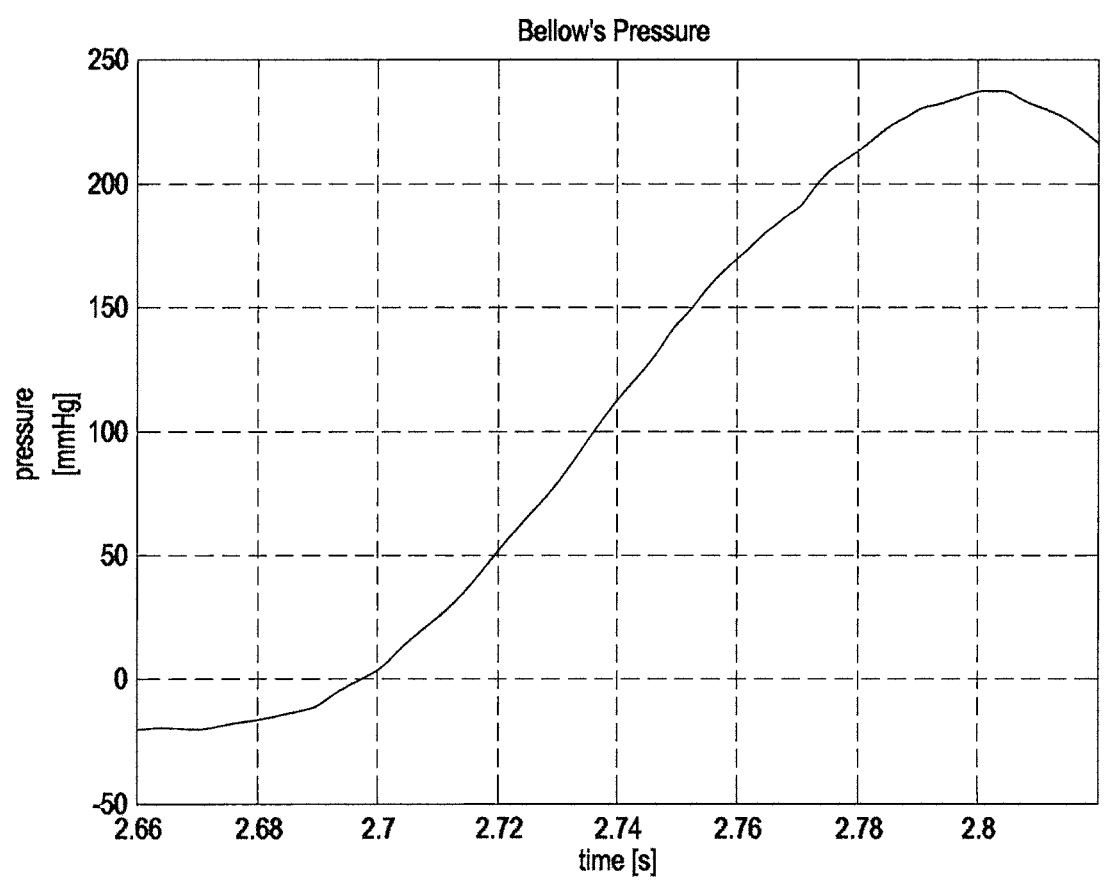
FIG. 16 is a graph showing pressure data generated via one embodiment of the device of the present invention.

FIG. 14 shows pressure data collected while the drive unit was operating in the closed pumping mode. From the compliance chamber data, the diastolic pressure of this experiment was 115 mmHg and the systolic pressure was ~150 mmHg. FIG. 15 displays the bellow's pressure data recorded between seconds 2.4 and 3.4 of the experiment. FIG. 16 displays the bellow's pressure data recorded between 2.66 and 2.82 s. The process of inflating the blood pump began at 2.67 s when the pressure started to increase. The inflation process ended at 2.80 s when the maximum pressure was reached. From this data, the bellows inflation time equaled 130 ms.

The blood pump inflation time can also be determined from FIG. 16. The volume of the blood pump remains zero until the pressure inside the bellows exceeds aortic pressure. From FIG. 16, the bellows pressure did not exceed the diastolic pressure of the compliance chamber until ~2.74 s. Inflation of the blood pump ended at 2.80 s when the maximum pressure was achieved. From this data, the blood pump inflation time equaled 60 ms.

Figure 17:
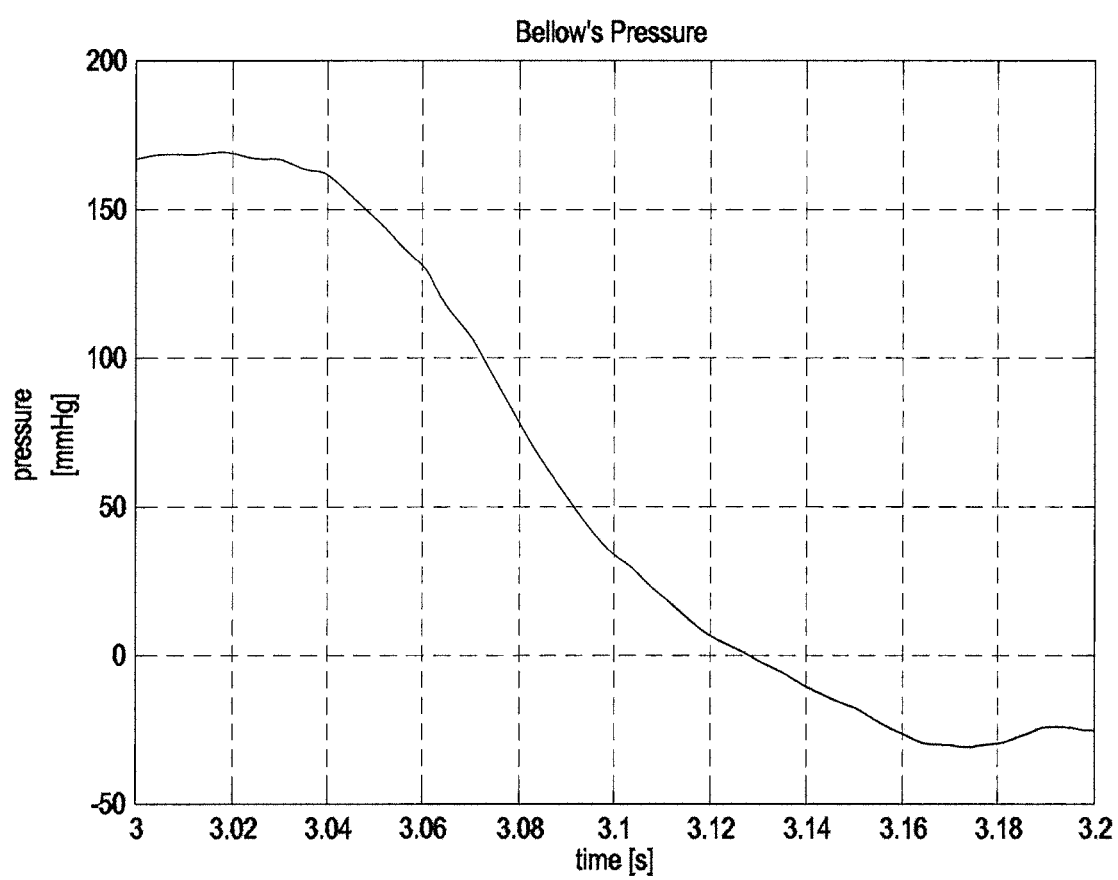
FIG. 17 is a graph showing pressure data generated via one embodiment of the device of the present invention during bellow deflation.

Deflation of the blood pump is shown in FIG. 17 where the bellow's pressure data is plotted during the expansion stroke of the bellows. Deflation began at 3.03 s when the pressure started to decrease. Deflation ended at 3.17 s when the pressure reached a minimum. The deflation process lasted 140 ms. The blood pump was observed to inflate and deflate correctly.

A further test was conducted to determine the bellows inflation time and the blood pump inflation time. A short bellows inflation time is required to follow high heart rates. Profusion of the coronary arteries is best augmented by minimizing the blood pump inflation time. Therefore, these additional tests studied the inflation and deflation times at two diastolic pressures: 80 and 120 mmHg. Eighty millimeters of mercury represents a normal diastolic pressure. A diastolic pressure of 120 mmHg tests the drive unit's ability to operate when the aortic pressure is abnormally high.

The results of the test are tabulated below in Table 1. All of the inflation and deflation times were less than the 160 ms listed in the specification documents. Increasing the diastolic pressure from 80 to 120 mmHg only increased the inflation and deflation times by 10 ms.

TABLE 1

|  |  | T |
| --- | --- | --- |
| Bellows inflation | 80 mmHg | 120 ms |
| Blood pump inflation | 80 mmHg | 70 ms |
| Bellows deflation | 80 mmHg | 130 ms |
| Bellows inflation | 120 mmHg | 130 ms |
| Blood pump inflation | 120 mmHg | 60 ms |
| Bellows deflation | 120 mmHg | 140 ms |

What is claimed is:

1. A skin interface device (SID) for an implantable cardiac assist device, comprising a processor, a non-transitory computer readable medium, and computer readable program code encoded in said non-transitory computer readable medium, the computer readable program code comprising a series of computer readable program steps to effect receiving signals from one or more implanted EKG sensors, the device further comprising circuitry operable to prevent an electric shock applied externally to the device from rendering the device inoperable.

2. The skin interface device of claim 1, said computer readable program code further comprising a series of computer readable program steps to effect:
   evaluating signals received from one or more implanted EKG sensors with reference to certain nominal signal characteristics encoded in computer readable program code; and
   rejecting signals received from one or more interconnected EKG sensors when those signals do not meet said nominal signal characteristics.

3. The skin interface device of claim 1, said computer readable program code further comprising a series of computer readable program steps to effect combining signals received from one or more implanted EKG sensors.

4. The skin interface device of claim 1, wherein the electric shock is generated by a defibrillator.

5. The skin interface device of claim 4, wherein the electric shock has a voltage of about 100, 200, 300, 400, 500, 600, 700, 800 or greater.

6. The skin interface device of claim 1, said computer readable program code further comprising a series of computer readable program steps to effect analyzing signals received from one or more implanted EKG sensors to detect a QRS complex.

7. The skin interface device of claim 1, further comprising data encoded in said non-transitory computer readable medium.

8. The skin interface device of claim 7, wherein the data comprises information regarding the operational status of the device.

9. The skin interface device of claim 8, wherein the data pertains to an error in operation of a component, timing or volume of fluid pumping, pumping pressure, or usage of a component.

10. The skin interface device of claim 7, wherein the data comprises information of status of the patient.

11. The skin interface device of claim 10, wherein data comprises patient medical history or a physiological parameter.

12. The skin interface device of claim 11, wherein the physiological parameter is selected from EKG signals, pulse, body temperature, blood pressure, a blood analyte concentration, or a combination thereof.

13. The skin interface device of claim 7, wherein the data comprises an event log or status log.

14. The skin interface device of claim 7, wherein data is collected and stored as a function of time.

15. The skin interface device of claim 1, wherein the device is operable for use with air as a pumping medium.

16. An arterial interface device for implantation into a subject, comprising:
   a body formed to include two lumens extending therethrough;
   wherein a first lumen formed in said body is configured to accept a pneumatic drive line interconnecting a partially implanted skin interface device and an implanted pump cardiac assist device, and wherein the skin interface device further comprises circuitry operable to prevent an electric shock applied externally to the device from rendering the device inoperable.

17. The arterial interface device of claim 16, further comprising:
   a pressure sensor;
   wherein a second lumen formed in said body is configured to house said pressure sensor.

18. The arterial interface device of claim 17, further comprising:
   a plurality of sensor leads extending outwardly from said body:
   wherein said plurality of sensor leads are configured to be attached to said partially implanted skin interfaced device.

19. The arterial interface device of claim 18, wherein said plurality of leads comprises:
   a power lead;
   a clock lead;
   a ground lead; and
   a data lead.

20. The arterial interface device of claim 16, wherein the device is operable for use with air as a pumping medium.

21. The arterial interface device of claim 16, wherein the electric shock is generated by a defibrillator.

22. The arterial interface device of claim 21, wherein the electric shock has a voltage of about 100, 200, 300, 400, 500, 600, 700, 800 or greater.

* * * * *